United States Patent [19]
Prager et al.

[11] Patent Number: 5,942,412
[45] Date of Patent: Aug. 24, 1999

[54] POLYNUCLEIC ACID ENCODING VARIANT INSULIN-LIKE GROWTH FACTOR I RECEPTOR BETA SUBUNIT AND RECEPTOR

[75] Inventors: Diane Prager; Shlomo Melmed, both of Los Angeles, Calif.

[73] Assignee: Cedars-Sinai Medical Center, Los Angeles, Calif.

[21] Appl. No.: 08/249,687

[22] Filed: May 26, 1994

Related U.S. Application Data

[63] Continuation of application No. 08/044,540, Apr. 6, 1993, abandoned.

[51] Int. Cl.$^6$ ............................. C12N 15/11; C12N 15/10
[52] U.S. Cl. .................... 435/69.1; 435/69.4; 435/252.3; 435/254.11; 435/320.1; 435/325; 435/440; 536/23.1; 536/23.51
[58] Field of Search ............................... 536/23.1, 23.51; 435/69.4, 69.1, 240.1, 242.3, 254.11, 320.1, 325, 252.3, 440

[56] References Cited

PUBLICATIONS

White, M.F., et al. "Mutation of the Insulin Receptor at Tyrosine 960 Inhibits Signal Transmission but Does Not Affect its Tyrosine Kinase Activity", *Cell*, 54:614–649, 1988.
Kapeller, R. et al., "Mutations in the Juxtamembrane Region of the Insulin Receptor Impair Activation of Phosphatidylinositol 3–Kinase by Insulin", *Molec. Endocrin.*, 5(6):769–777 (1991).
Yamasaki, H. et al., "Pituitary Insulin–like Growth Factor I Receptor Signaling: Critical Role of Receptor Beta Subunit $^{950}$Tyrosine for Insulin–Like Growth Factor I Signal Transduction", *Clinical Research*, 40(1):24A, (1992).
Thies et al., J. of Biol. Chem., 265, 10132–10137, Jun. 15, 1990.
Rajagopalan et al., J. Biol. Chem., 266, 23068–23073, Dec. 5, 1991.
Ellis et al., Cell, vol. 45, pp. 721–732, 1986.
McClain et al., J. Biol. Chem., vol. 262, 14663, 1987.
Ullrich et al., Embo Journal, vol. 5, 2503, 1986.
Yamasaki, et al., "Structure–Function of the Human Insulin–Like Growth Factor–I Receptor: A Discordance of Somatotroph Internalization and Signaling." *Mol. Endocrinology*, vol. 7: 681–685 (1993).
Pietrzkowski, et al., "Inhibition of Cellular Proliferation by Peptide Analogues of Insulin–like Growth Factor $1^1$," Cancer Research, vol. 52 (Dec. 1, 1992), pp. 6447–6451.
Krane, et al., "The Insulin–like Growth Factor I Receptor Is Overexpressed in Psoriatic Epidermis, but Is Differentially Regulated from the Epidermal Growth Factor Receptor," J. Exp. Med., vol. 175 Apr. 1992, pp. 1081–1090.
Pietrzkowski, et al., "Inhibition of Growth of Prostatic Cancer Cell Lines by Peptide Analogues of Insulin–like Growth Factor $1^1$," Cancer Research, vol. 53, Mar. 1, 1993, pp. 1102–1106.

Kato, et al., "Role of Tyrosine Kinase Activity in Signal Transduction by the Insulin–like Growth Factor–I (IGF–I) Receptor," The Journal of Biological Chemistry, vol. 268, No. 4, Feb. 5, 1993, pp. 2655–2661.
Xiong, et al., "Growth–stimulatory monoclonal antibodies against human insulin–like growth factor I receptor," Proc. Natl. Acad. Sci. USA, vol. 89, Jun. 1992, pp. 5356–5360.
Siegfried, et al., "A mitogenic peptide amide encoded within the E peptide domain of the insulin–like growth factor IB prohormone," Proc. Natl. Acad. Sci. USA, vol. 89, Sep. 1992, pp. 8107–8111.
Herskowitz, "Functional inactivation of genes by dominant negative mutations," Nature, vol. 329, Sep. 17, 1987, pp. 219–222.
Moxham, et al., "Insulin–like Growth Factor I Receptor–Subunit Heterogeneity" The Journal of Biological Chemistry, vol. 264, No. 22, Aug. 5, 1989, pp. 13238–13244.
Yamasaki, et al., "Insulin–Like Growth Factor–I (IGF–I) Attenuation of Growth Hormone is Enhanced by Overexpression of Pituitary IGF–I Receptors," Molecular Endocrinology, vol. 5, No. 7, 1991, pp. 890–896.
Soos, et al., "Receptors for insulin and insulin–like growth factor–I can form hybrid dimers," Biochem. J., vol. 270, 1990, pp. 383–390.
Maegawa, et al., "Insulin Receptors with Defective Tyrosine Kinase Inhibit Normal Receptor Function at the Level of Substrate Phosphorylation," The Journal of Biological Chemistry, vol. 263, No. 25, Sep. 5, 1988, pp. 12629–12637.
Prager, et al., "Human Insulin–like Growth Factor I Receptor Function in Pituitary Cells Is Suppressed by a Dominant Negative Mutant," J. Clin. Invest, vol. 90, Nov. 1992, pp. 2117–2122.
Osborne, et al., "Regulation of Breast Cancer Growth By Insulin–like Growth Factors," J. Steroid Biochem. Molec. Biol., vol. 37, No. 6 1990, pp. 805–809.
Pollak, et al., Tamoxifen reduces Serum insulin–like growth factor I (IGF–I), Breast Cancer Research and Treatment, vol. 22, 1992, pp. 91–100.
Polychronakos, et al., "Mitogenic Effects of Insulin and Insulin–like Growth Factors on PA–III Rat Prostate Adenocarcinoma Cells: Characterization of the Receptors Involved," The Prostate, vol. 19, 1991, pp. 313–321.
Yamasaki, et al., "Human Insulin–like Growth Factor I Receptor$^{950}$ Tyrosine Is Required for Somatotroph Growth Factor Signal Transduction," The Journal of Biological Chemistry, vol. 267, No. 29, Oct. 15, 1992, pp. 20953–20958.

*Primary Examiner*—Sally P. Teng
*Attorney, Agent, or Firm*—Pretty, Schroeder & Poplawski

[57] ABSTRACT

The present invention provides novel IGF-I receptor subunits characterized by modified IGF-I receptor function, novel polynucleic acid sequences that encode these receptor subunits, and various applications for their use.

55 Claims, 1 Drawing Sheet

POLYNUCLEIC ACID ENCODING VARIANT INSULIN-LIKE GROWTH FACTOR I RECEPTOR BETA SUBUNIT AND RECEPTOR

This application is a continuation of application Ser. No. 08/044,540 filed Apr. 6, 1993, now abandoned.

ACKNOWLEDGEMENT

The invention was made with Government support under Grant Numbers DK34824 and DK02023, awarded by the National Institute of Health. The Government may have certain rights in the invention.

FIELD OF THE INVENTION

The present invention relates to insulin-like growth factor-I and its receptor, and more particularly relates to insulin-like growth factor-I receptor subunits and receptors having modified tyrosine kinase activity, as well as methods for use thereof.

BACKGROUND OF THE INVENTION

Insulin-like growth factor (IGF-I) is a 7.5-kD polypeptide that circulates in plasma in high concentrations and is detectable in most tissues. IGF-I is predominantly a mitogenic factor for a variety of cell and tissue types, but also stimulates cell differentiation and cell proliferation. The importance of IGF-I to growth of tissues is suggested by increasing plasma concentrations throughout adolescence, reaching a plateau in adults, and in the requirement of most mammalian cell types for IGF-I for sustained proliferation. For a review of the wide variety of cell types for which IGF-I/IGF-I receptor interaction mediates cell proliferation, see Goldring, M. B. and Goldring, S. R., *Eukar. Gene Expression*, 1:31–326 (1991).

In vivo, serum levels of IGF-I are dependent on pituitary growth hormone(GH). Although the liver is a major site of growth hormone-dependent IGF-I synthesis, recent work indicates that the majority of normal tissues also produce IGF-I. A variety of neoplastic tissues may also produce IGF-I. Thus IGF-I may act as a regulator of normal and abnormal cellular proliferation via autocrine or paracrine, as well as endocrine mechanisms.

The first step in the transduction pathway leading to IGF-I-stimulated cellular proliferation is binding of receptor ligand (IGF-I, IGF-II, or insulin at supraphysiological concentrations) to IGF-I receptor. The IGF-I receptor is composed of two types of subunits: an alpha subunit (a 130–135 kD protein that is entirely extracellular and functions in ligand binding) and a beta subunit (a 95-kD transmembrane protein, with transmembrane and cytoplasmic domains). The IGF-I receptor is initially synthesized as a single chain proreceptor polypeptide which is processed by glycosylation, proteolytic cleavage, and covalent bonding to assemble into a mature 460-kD heterotetramer comprising two alpha-subunits and two beta-subunits. The beta subunit (s) possesses ligand-activated tyrosine kinase activity. This activity is implicated in the signaling pathways mediating ligand action which involve autophosphorylation of the beta-subunit and phosphorylation of IGF-I receptor substrates.

Thus the IGF-I receptor is seen to play a pivotal role in normal and abnormal proliferative processes. Enhanced IGF-I levels are correlated with several, diverse pathological states, including acromegaly, gigantism. Abnormal IGF-I/ IGF-I receptor function has been implicated in psoriasis, diabetes (microvascular proliferation), smooth muscle restenosis of blood vessels following angioplasty. In a variety of cancers, such as leukemia, lung cancer, ovarian cancer and prostate cancer, there is overexpression of the IGF-I receptor by the tumor tissue relative to the non-cancerous tissue, possibly implicating IGF-I/IGF-I receptor interaction in an autocrine or paracrine feedback loop resulting in autonomous proliferation of the tissue. For a review of the role IGF-I/IGF-I receptor interaction plays in the growth of a variety of human tumors, see Macaulay, V. M., *Br. J. Cancer*, 65: 311–320 (1992).

Potential strategies for the inhibition of cell proliferation associated with such pathologies include suppressing IGF-I levels or interrupting IGF-I action at the level of its cellular receptor. For example, drugs have been employed to reduce IGF synthesis and/or secretion. These include the long acting somatostatin analogue octreotide for treatment of endocrine tumors including carcinoid, and experimentally for the treatment of acromegaly and breast cancer, and tamoxifen for the treatment of breast cancer. However, there has been an inherent difficulty in suppressing circulating IGF-I to levels such that tissue concentrations become limiting to cell growth, especially without affecting normal growth of non-targeted tissue.

One strategy for interrupting IGF-I action at the level of its cellular receptor employs antibodies to the IGF-I receptor. However, it has been reported that these antibodies can be stimulatory rather than antagonistic over time. There is, therefore, a clear need in the art for methods of modifying ligand activated IGF-I receptor function at the cellular level. Preferably such methods would enable inheritable modifications of IGF-I receptor function in the cells of target tissue without disrupting the endogenous IGF-I receptor function in cells of nontargeted tissue.

BRIEF DESCRIPTION OF THE INVENTION

The present invention provides novel polynucleic acids comprising a sequence encoding an IGF-I receptor subunit (s) having modified IGF-I receptor function relative to endogenous IGF-I receptor, and the polypeptides encoded thereby. The IGF-I receptor subunit(s) encoded by the polynucleic acids of the present invention may correspond to either the beta subunit or the alpha and beta subunits of the IGF-I receptor. One IGF-I receptor function which may be modified is tyrosine kinase activity. Tyrosine kinase activity includes autophosphorylation and phosphorylation of cytosolic IGF-I receptor substrate, either one, or both of which may be modified in accordance with the present invention.

Variant IGF-I receptors provided by the present invention are characterized by modified IGF-I receptor function, for example modified tyrosine kinase activity, relative to endogenous IGF-I receptor, and are typically assembled from at least one variant beta subunit to form a variant IGF-I receptor heterotetramer. Alternatively, variant IGF-I receptor may be assembled from two variant beta subunits.

The present invention also provides methods of inhibiting endogenous IGF-I receptor function using the novel polynucleic acids and polypeptides of the present invention.

DETAILED DESCRIPTION OF THE INVENTION

Figure 1:
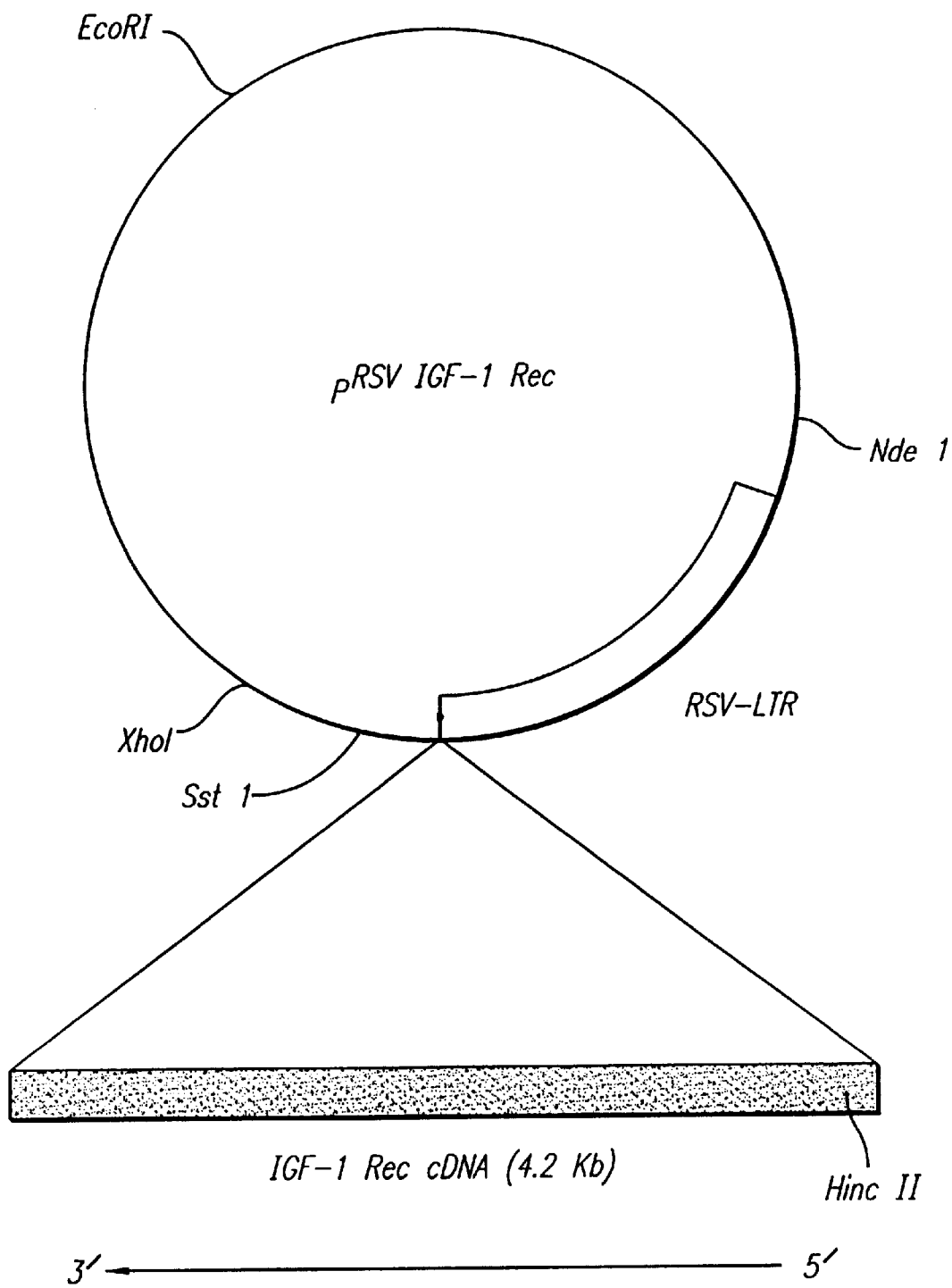
FIG. 1 is a schematic diagram of the pRSV-IGFIR plasmid used for transfection of target cells. An 4.2 kb HincII/Sst1 fragment of the human IGF-I receptor cDNA was cloned into expression vector Rexp.

The present invention provides novel IGF-I receptor subunits characterized by modified IGF-I receptor function, novel polynucleic acid sequences that encode these receptor subunits, and various applications for their use.

The activation of the IGF-I receptor by its ligands plays a central role in the proliferation of a wide variety of cell types and is implicated in the progression of many diseases. Efforts directed to treating diseases associated with high levels of cellular IGF-I have met with limited success as they have focused on either lowering serum concentrations of IGF-I or obstructing IGF-I binding to IGF-I receptor. The present invention avoids the inherent difficulties associated with these strategies and provides an inheritable, tissue-specific method of modifying ligand activated IGF-I receptor function at the cellular level.

IGF-I receptor has several functional sites, for example, ligand binding, substrate-binding, autophosphorylation, phosphorylation of substrate, membrane association, binding between the subunits, and so on. Generally speaking, it has been discovered that one or more functions of IGF-I receptor can be independently modified (i.e., by selective mutation of nucleic acid encoding the IGF-I receptor subunit (s)) without significantly disrupting the other functions of the receptor.

Exploiting this phenomenon, variants of endogenous IGF-I receptors may be formed by selectively mutating that portion of a nucleotide sequence which encodes for the function of interest. The resulting variant subunits maintain their ability to complex with either endogenous IGF-I receptor subunits or other variant IGF-I receptor subunits to form variant IGF-I receptors. When the variant IGF-I receptor subunit is present in the target cell, the target cell exhibits the phenotype characteristic of the variant IGF-I receptor subunit in a dominant negative fashion.

The phenotype characteristic of the variant subunit and receptor is referred to as "dominant" because it is manifested even in the presence of the endogenous gene. The phenotype of the variant subunit and receptor is referred to as "negative" because it is antagonistic to the phenotype of the endogenous IGF-I receptor. Use of the dominant negative terminology, however, is not intended to exclude the desired phenotype which may result from competition due to the presence of a large number of variant subunits in the cell.

Thus, the methods of the present invention employ recombinant nucleic acid technology to express variant IGF-I receptor subunit. Expression of variant subunit exerts a dominant negative effect on endogenous IGF-I receptor subunits and produces the desired phenotype in the targeted cells, as well as their progeny.

In accordance with the present invention, there is provided a recombinant polynucleic acid comprising a sequence encoding IGF-I receptor subunit(s). The encoded IGF-I receptor subunit(s) is characterized by modified IGF-I receptor function relative to the IGF-I receptor function of endogenous IGF-I receptor.

The term "polynucleic acid" is intended to include deoxyribonucleic acid and ribonucleic acid in all their forms, i.e., double-stranded DNA, cDNA, mRNA and the like. Polynucleic acid sequences encoding IGF-I receptor subunit(s) may encode none, part or all of the alpha subunit of the IGF-I receptor. In a presently preferred embodiment of the invention, polynucleic acid sequences encode both the alpha and the beta subunits of the IGF-I receptor with appropriate mutations to achieve modified tyrosine kinase activity.

The term "IGF-I receptor function" is intended to include IGF-I receptor function associated with both disease and non-diseased states, for example, tyrosine kinase activity, ligand binding, internalization of ligand, ATP binding, binding of cytoplasmic substrate, ligand-dependent cell differentiation, ligand-dependent cell proliferation, ligand-dependent cell transformation, ligand-dependent cell tumorigenesis, and the like. The term "ligand-dependent" is used herein to indicate that the IGF-I receptor function is dependent upon binding of ligand to the IGF-I receptor to activate the function.

The term "modified" as used to modify "IGF-I receptor function" or "tyrosine kinase activity" or any one of the IGF-I receptor functions, refers to an increase, decrease, change in pattern or absence of that function relative to the function of endogenous IGF-I receptor.

As used herein, the term "endogenous IGF-I receptor" is intended to mean IGF-I receptor native to the cell of interest. The term "endogenous IGF-I receptor subunit" as used herein is intended to mean the alpha and/or the beta subunit of the IGF-I receptor native to the cell.

In accordance with the present invention, there also provided a recombinant polynucleic acid comprising a sequence encoding IGF-I receptor subunit(s) wherein the encoded IGF-I receptor subunit(s) is characterized by modified tyrosine kinase activity relative to the tyrosine kinase activity of endogenous IGF-I receptor subunit.

The term "modified tyrosine kinase activity" as used herein, refers to an increase, decrease, change in pattern or absence of tyrosine kinase activity relative to the tyrosine kinase activity of endogenous IGF-I receptor. The term "tyrosine kinase activity" includes autophosphorylation of the IGF-I receptor and phosphorylation of cytoplasmic substrate i.e., IRS-1, P13 kinase, pp185, and the like.

Set forth as SEQ ID NO: 1 is a DNA sequence representing a cDNA clone encoding alpha and beta subunits of human IGF-I receptor. Set forth as SEQ ID NO: 2 is the deduced amino acid sequence encoded by SEQ ID NO: 1. Nucleotides 32 through 121 encode the signal sequence. Nucleotides 122 through 2239, and amino acids 1 through 706 encode the alpha subunit. Nucleotides 2252 through 4132, and amino acids 711 through 1337 encode the beta subunit.

The alpha and beta subunits of mature IGF-I receptor are linked by a disulfide bond. With reference to SEQ ID NO: 2 this binding site on the beta subunit is within amino acids 744 through about 906. The beta subunit can be further described as having a transmembrane region at or about amino acid residues 906 through about 929 of SEQ ID NO: 2. The beta subunit also has a juxta-membrane region adjacent to the transmembrane region at amino acid residues 930 through about 972. When the mature IGF-I receptor is anchored in the cell membrane, the juxta-membrane region is located within the cytosol adjacent to the cell membrane. Further downstream of the juxta-membrane region on the beta subunit is the ATP binding domain at about amino acid residue 1003. Between the ATP binding site and the carboxy terminus at amino acid 1337, lies the cytosolic tyrosine kinase domain at about amino acid residues 973–1229.

In another embodiment of the present invention, the nucleic acid sequence of endogenous IGF-I receptor subunit, or a nucleic acid sequence that is compatible with the target cell and encodes IGF-I receptor subunit, is modified, for example, by mutation such that the expressed IGF-I receptor subunit has modified IGF-I receptor function. Of course, the location chosen for mutation will depend upon the function of the endogenous IGF-I receptor which one desires to modify. The juxta-membrane region, for example at amino acid residues 943, 950 and 957, the ATP binding site, for example at residue 1003, and the cytosolic tyrosine kinase domain, for example, at amino acid residues 1131, 1135 and 1136 and the carboxy terminus at amino acid residue 1337 are all amenable to amino acid substitutions to modify tyrosine kinase activity. In addition, truncation of the beta subunit by insertion of an inframe stop codon (UAG, UAA or UGA), for example, at amino acid residue 952 of the beta subunit, as well as a 22 amino acid residue deletion of amino acids 943 through 966, results in modified tyrosine kinase activity. Details of the mutations to the beta subunit referenced above are described in greater detail in the Examples provided below. Using the information provided in the present disclosure, one of skill in the art will appreciate that there are many other ways, well known to those of skill in the art, to mutate the nucleic acid sequence, or alter the amino acid sequence to achieve the desired result, including any one of a number of missense or nonsense mutations.

In a presently preferred embodiment, only that portion of the beta subunit necessary for binding the alpha subunit to form a mature IGF-I receptor tetramer, and only that portion of the beta subunit necessary to anchor the IGF-I receptor subunit in the cell membrane is encoded by the polynucleic acid sequences and amino acid sequences of the present invention. For example, the nucleic acid sequences and the amino acid sequences may only encode the amino-terminus of the beta subunit through that portion of the transmembrane domain necessary to achieve anchorage, i.e., nucleatides residue 2252 through about 2909.

The phrase "substantially the same" is used herein in reference to nucleic acid sequences or amino acid sequences that have non-consequential sequence variations from SEQ ID NO: 1 and SEQ ID NO: 2, respectively, other than those variations necessary to achieve modified IGF-I receptor function in accordance with the present invention. For example, the nucleotide sequences and amino acid sequences resulting from the mutations to human IGF-I receptor cDNA as described in Example II would be substantially the same as SEQ ID NO: 1. Likewise, the amino acid sequences resulting from expression of these mutant human IGF-I receptor cDNA would be substantially the same as SEQ ID NO: 2. Similarly, changes in nucleotide sequences or amino acid sequences that result in substitution of a charged residue for a similarly charged residue or substitution of a non-polar residue for another non-polar residue that does not substantially alter the function of the IGF-I receptor subunit (except as provided above) or its tertiary structure would be "substantially the same" sequence.

In yet another embodiment of the present invention there is provided a polynucleic acid comprising a sequence encoding an IGF-I receptor subunit characterized by modified IGF-I receptor function, for example, modified tyrosine kinase activity, relative to endogenous IGF-I receptor function, and further characterized by its ability to complex with endogenous IGF-I receptor subunit(s) to form variant IGF-I receptors.

The term "variant IGF-I receptor" as used herein refers to a mature IGF-I receptor having a tetrameric structure comprised of two alpha subunits and two beta subunits, wherein at least one of the beta subunits is a variant IGF-I receptor subunit and the receptor has a desired dominant phenotype, usually antagonistic to the phenotype of the endogenous IGF-I receptor.

The term "variant IGF-I receptor subunit" as used herein is intended to mean an IGF-I receptor subunit exhibiting modified IGF-I receptor function relative to endogenous IGF-I receptor function, when the variant IGF-I receptor subunit is a constituent of the variant IGF-I receptor. For example, a variant IGF-I receptor subunit may exhibit modified tyrosine kinase activity relative to endogenous IGF-I receptor subunit. A variant IGF-I receptor subunit may be further characterized by its ability to complex with endogenous IGF-I receptor subunit(s) to form a variant IGF-I receptor.

In still another embodiment of the present invention, there are provided vectors containing the nucleic acids of the present invention. As used herein, "vector" or "plasmid" refers to discrete elements that are used to introduce polynucleic acid sequences of the present invention into cells for either expression or replication. Selection and use of such vectors are well known to those of skill in the art and will vary in accordance with the cell targeted to receive the polynucleic acid.

An expression vector includes constructs capable of expressing polynucleic acid sequences that are operatively linked with regulatory sequences, such as promoter regions. Thus, an "expression vector" refers to a recombinant DNA or RNA construct, such as a plasmid, a phage, recombinant virus or other vector that, upon introduction into an appropriate host cell, results in expression of the cloned polynucleic acid sequence. Appropriate expression vectors are well known to those of skill in the art and include those that are replicable in eukaryotic cells and/or prokaryotic cells and those that remain episomal or those which integrate into the host cell genome. Presently preferred plasmids for expression of variant IGF-I receptor subunits in eukaryotic host cells, particularly mammalian cells, include Rexp with an RSV LTR, Moloney murine leukemia virus LTR driven expression vector, and the like.

As used herein, a promoter region refers to a segment of polynucleic acid that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. Promoters, depending upon the nature of the regulation, may be constitutive or regulated. For example, promoters contemplated for use in the practice of the present invention include the SV40 early promoter, the cytomegalovirus (CMV) promoter, Moloney murine leukemia virus (MMLV) promoter, thymidine kinase promoter, Rous sarcoma virus promoter (RSV), and the like.

As used herein, the term "operatively linked" refers to the functional relationship of polynucleic acid sequences with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

In accordance with another embodiment of the present invention, there are provided cells containing the above-described polynucleic acids. Such host cells as bacterial, yeast and mammalian cells can be used for replicating polynucleic acids of the present invention and producing variant IGF-I receptor subunit(s). Incorporation of cloned polynucleic acid into a suitable expression vector, transfection of eukaryotic cells with a plasmid vector or a combination of plasmid vectors or with linear DNA, or infection with retroviral constructs, and selection of transfected or infected cells are well known in the art (see, Sambrook et al. *Molecular Cloning: A Laboratory Manual*, Second Edition, Cold Spring Harbor (1989). Heterologous DNA may be introduced into host cells by any method known to those of skill in the art, such as transfection with a vector encoding the heterologous DNA by $CaPO_4$ precipitation (See, e.g., Kashanchi, F., et al. *Nucleic Acids Research*, 20:4673–4674 (1992). This same method can be used to introduce the proteins of the present invention into host cells.) Recombinant cells can then be cultured under conditions whereby the subunit(s) encoded by the DNA is expressed. Preferred cells include mammalian cells, such as for example, tumor cells, lymphocytes, stem cells, pituitary cells, bone marrow cells, fibroblasts and the like.

In yet another embodiment of the present invention there are provided polypeptides encoded by the nucleic acids of the present invention. As used herein, the words "protein", "peptide" and "polypeptide" are considered to be equivalent terms and are used interchangeably.

In addition to polynucleic acids and protein compositions of matter, several novel methods of using the polynucleic acids and polypeptides of the present invention are provided. The present invention provides methods inhibiting endogenous IGF-I receptor function in a cell by introducing into the cell, variant IGF-I receptor subunit under conditions suitable to form a variant IGF-I receptor, wherein said variant receptor is characterized by modified tyrosine kinase activity relative to endogenous IGF-I receptor tyrosine kinase activity. In will be understood that the methods of the present invention may be performed in vitro, as well.

In accordance with the methods of the present invention, the nucleic acid sequences encoding variant IGF-I receptor subunit can be administered to mammals as a therapeutic agent by any means known to those of skill in the art, including intraperitoneal, subcutaneous, intravascular, intramuscular, intranasal or intravenous injection, implant or transdermal modes of administration, and the like. One of skill in the art will appreciate that when the compositions of the present invention are administered as therapeutic agents, it may be necessary to combine the compositions with a suitable pharmaceutical carrier. The choice of pharmaceutical carrier and the preparation of the composition as a therapeutic agent will depend on the intended use and mode of administration. Suitable formulations and methods of administration of therapeutic agents can readily be determined by one of skill in the art.

The dosage regimen for treating IGF-I associated disorders depends on a variety of factors, including type of disorder, age, weight, sex and medical condition of the patient, as well as the severity of the pathology, the route of administration, and the type of therapeutic agent used. A skilled physician or veterinarian can readily determine and prescribe the effective amount of the compound or pharmaceutical required to treat the patient. Conventionally, one of skill in the art would employ relatively low doses initially and subsequently increase the dose until a maximum response is obtained. Because the nucleic acids of the present invention are susceptible to amplification, much lower doses are believed to be effective than with conventional methods of administering drugs.

The invention will now be described in greater detail by reference to the following non-limiting examples.

EXAMPLE I

Plasmid Construction

Standard techniques for DNA manipulations as described by Sambrook J. et al., *Molecular Cloning—A Laboratory Manual*, Second Edition, Cold Spring Harbor (1989) were used for all plasmid constructions. The 4.2-kb cDNA fragment encoding human IGF-I receptor used in the following examples was obtained by screening a human HeLa cell cDNA library (Stratagene, La Jolla, Calif.) with a DNA fragment of SEQ ID NO: 1 (nucleic acid residues 43 through 280) and an oligonucleotide probe as described in Ullrich A., et al. EMBOJ, 5:2503–2512 (1986) and set forth in SEQ ID NO: 14. This oligonucleotide was synthesized on an ABI #394 DNA Synthesizer (Applied Biosystems, Inc. Foster City, Calif.). Specific clones were selected by three rounds of sequence specific colony hybridization with $^{32}$P-labelled oligonucleotide and DNA fragment probes. Overlapping clones were ligated together to yield a full length clone whose identity was confirmed by DNA sequencing.

Expression constructs were prepared by ligating the 4.2-kb Hincll-SstI fragment of the isolated human IGF-I receptor cDNA into the polylinker site of the mammalian expression vector Rexp (See. FIG. 1). Rexp is described in Yamasaki, H. et al., *Mol. Endocrinology* 5:890 (1991) and was obtained from M. Rosenfeld, at the University of California, San Diego, Calif. A construct in the forward orientation was identified by restriction mapping and was designated pRSV-IGFIR.

A construct in the reverse orientation, generated by ligating the BamHl fragment of the human IGF-I receptor cDNA into BamHl site of Rexp expression vector was designated pRSV-rIGFIR. All plasmids were purified over two cesium chloride gradients.

EXAMPLE II

Mutagenesis of the Human IGF-I Receptor cDNA

A 0.45 kb SmaI-HindIII fragment from pRSV-IGFIR was subcloned into M13mp19. The following primers were utilized for mutagenesis, 5'-CTGGGGAATGCTGTGCTGTAT-3' ($^{940}$Gly→$^{940}$Ala; SEQ ID NO:3), 5'-AATGGAGTGCTAGCTGCCTCTGTG-3' ($^{943}$Tyr→$^{943}$Ala; SEQ ID NO:4), 5'-AACCCGGAGTGTTTCAGCGCT-3' ($^{950}$Tyr→$^{950}$Cys; SEQ ID NO:5), 5'-AACCCGGAGTCATTCAGCGCT-3' ($^{950}$Tyr→$^{950}$Ser; SEQ ID NO:6), 5'-AACCCGGAGGCTTTCAGCGCT-3' ($^{950}$Tyr→$^{950}$Ala; SEQ ID NO:7), 5'-AACCCGGAGCTATTCAGCGCT-3' ($^{950}$Tyr→$^{950}$Leu; SEQ ID NO:8), 5'-AACCCGGAGACATTCAGCGCT-3' ($^{950}$Tyr→$^{950}$Thr; SEQ ID NO:9), 5'-GCTGATGTGGCTGTTCCTGAT-3' ($^{957}$Tyr→$^{957}$Ala; SEQ ID NO:10), 5'-GTGGCCATTGCTACAGTGAAC-3' ($^{1003}$Lys→$^{1003}$Ala; SEQ ID NO:11), and 5'-GGGAATGGAGTGCTGTATCGGGAGAAGATCAC-CATGAGC-3' (22 amino acid deletion; SEQ ID NO:12).

Mutagenizing oligonucleotides were annealed to single-stranded DNA, and subsequent mutagenesis was performed utilizing an Amersham kit according to the manufacturer's instructions. A SalI linker (5'-GTCGAC-3') was inserted into the ScaI site of SmaI-HindIII fragment encoding the IGF-I receptor, producing IGFIR-CRH which contains three additional amino acids (Cys-Arg-His) inserted at position 950. For truncation of the human IGF-I receptor, the 0.45 kb Sma-HindIII fragment was subcloned into M13mp19. An Xba linker, 5'TGCTCTAGAGCA3' (SEQ ID NO: 13) was inserted into the ScaI site present in a SmaI-HindIII IGF-I receptor cDNA fragment, producing an in-frame stop codon at position 952.

After reintroduction of the mutant sequences into the pRSV-IGFIR vector, all constructs were subjected to dideoxy sequencing utilizing T7 sequenase (U.S. Biochemical, Cleveland, Ohio) to confirm the mutant sequences. Plasmids containing cDNA encoding the following wild type and the following variant IGF-I receptor subunits were formed:

WT=human IGF-I receptor subunit without mutation;

$^{940}$Ala=human IGF-I receptor subunit with alanine substitution at residue 940 in the juxta-membrane region;

$^{943}$Ala=human IGF-I receptor subunit with alanine substitution at residue 943 in the juxta-membrane region;

$^{950}$Cys=human IGF-I receptor subunit with cysteine substitution at residue 950 in the juxta-membrane region;

$^{950}$ser=human IGF-I receptor subunit with serine substitution at residue 950 in the juxta-membrane region;

$^{950}$Leu=human IGF-I receptor subunit with leucine substitution at residue 950 in the juxta-membrane region;

$^{950}$Thr=human IGF-I receptor subunit with threonine at residue 950 in the juxta-membrane region;

$^{952}$STOP=human IGF-I receptor subunit having a truncated beta subunit;

$^{957}$Ala=human IGF-I receptor subunit with alanine substitution at residue 957 in the juxta-membrane region;

$^{1003}$Ala human IGF-I receptor subunit with alanine substitution at residue 1003 in the ATP binding domain;

Δ22=human IGF-I receptor subunit with 22 amino acid deletion at residues 943 through 966; and IGFIR-CRH=human IGF-I receptor subunit having three additional amino acids (Cys-Arg-His) inserted at residue 950.

All plasmids were purified on two cesium chloride gradients.

EXAMPLE III

Transfection of GC Rat Pituitary Cells and Rat I Fibroblasts

GC rat pituitary cells (GC cells) secreting growth hormone were obtained from Dr. H. H. Samuels, New York N.Y., but may be obtained from a variety of commercially available sources. GC rat pituitary cells were grown at 37°C. in a humidified atmosphere of 95% air/5% $CO_2$ in Dulbecco's Modified Eagle's Medium (DMEM) supplemented with 10% (vol/vol) fetal calf serum.

Rat I fibroblasts were obtained from P. Koeffler (Cedars-Sinai Medical Center, Los Angeles Calif.), but may be obtained from a variety of commercially available sources. Rat I fibroblast were grown at 37° C. in αMEM supplemented with 10 (vol/vol) fetal calf serum.

Semiconfluent GC cells or Rat I fibroblasts were cotransfected for 24 hours with 10 μg of linearized vector pRSV-IGFIR or pRSV-rIGFIR (plasmid mutants described in Example II; Rat I fibroblasts were only transfected with WT or $^{952}$STOP and 1 μg pSV2neo to allow for neomycin-resistant selection (described by Southern P.J. et al., in *J. Mol. Appl. Genet.*, 1:327–341 (1982). Transfections were performed by the calcium phosphate coprecipitation method, as described by Prager, D. et al., *J. Biol. Chem.* 263:16580–16585 (1988).

Cells were then split 1:6 and neomycin (G418; Gibco, Gaithersburg, Md.) was added in fresh medium at a concentration of 400 μg/ml to GC cells and 600 μg/ml to Rat I fibroblasts. Medium was replenished every 72 hours. G418-resistant colonies were subcloned and further characterized. Mock transfected Rat I cells (I51Neo i.e., human IGF-I receptor cDNA and pSV2neo integrated) having no expression of human IGF-I receptor on the cell surface were utilized as controls.

EXAMPLE IV

Variant IGF-I Receptors Bind IGF-I

Binding of radiolabeled IGF-I was performed in suspension. About $1 \times 10^6$ transfected GC cells or Rat I fibroblasts were incubated with [$^{125}$I] IGF-I (50,000 cpm, specific activity 2,000 Ci/mmol) (Amersham, Arlington Heights, Ill.). Increasing concentrations of unlabeled recombinant human IGF-I (Met-59) (Fujisawa Pharmaceuticals Co., Osaka, Japan) in a final volume of 1 ml binding buffer (50 mM HEPES (pH 8) containing 1% bovine serum albumin, 120 mM or 150 mM NaCl, 1.2 mM $MgSO_4$) at about 15° C. were added. Non-specific binding was defined as binding observed in the presence of excess (100 nM) unlabeled IGF-I.

After 3 hours incubation, transfectants were centrifuged and cell-associated radioactivity was separated from free [$^{125}$I] IGF-I by adding 300 μl of ice-cold dibutylphthalate. Cell-associated radioactivity of the samples was then determined by gamma-counting. Calculation of total bound ligand included the free-labeled ligand.

Increasing amounts of unlabeled IGF-I displaced GC cell-associated [$^{125}$I] IGF-I binding to all transfectants, with 50% displacement of maximum binding achieved by 0.6–2 nM IGF-I. When these binding displacement data were subjected to Scatchard analysis, a linear plot was obtained for all mutant transfectants, indicating the presence of a single class of high affinity receptors in these GC transfectants. The derived association constant (Kd) for [$^{125}$I] IGF-I binding was similar in all transfectants, ranging from 0.25 to 0.66 nM, except for $^{940}$Ala which had 1.19 nM Kd. This similarity of ligand affinity for the different mutant receptors is expected, because the configuration of the extracellular alpha subunit is expected to remain intact when the beta subunit was mutated. The derived number of variant IGF-I receptors present on each transfectant was increased from 7- to 34-fold compared to untransfected cells.

Likewise, Scatchard analysis of the transfected Rat I fibroblast clones selected for further study revealed that although binding affinities for the intact human IGF-I receptor WT cDNA transfectants and truncated human IGF-I receptor cDNA transfectants $^{952}$ (STOP) (1.08 and 0.67nM, respectively) were similar to the Kd for IGF-I binding to untransfected Rat 1 fibroblasts, transfectants exhibited a 2.5–7 fold increase in IGF-I binding sites/cell.

In summary, expression of variant human IGF-I receptor subunit cDNA in GC cells and Rat I fibroblasts results in an increase in IGF-I binding sites per cell. The increase in binding sites is attributable to the formation of variant IGF-I receptors.

EXAMPLE V

Integration of Variant DNA Into Host Genome

To confirm integration of exogenous human IGF-I receptor DNA into GC cell and Rat I fibroblast genomic DNA, Southern blot analysis of transfected cell DNA was performed.

Genomic DNA isolated from transfected and untransfected cells was prepared as described by Prager, D. et al., *J. Clin. Invest.*, 85:1680–1685 (1990) and digested with BamHI or EcoRI (Bethesda Research Laboratories, Gaithersburg, Md.). The DNA fragments were separated by electrophoresis on an 0.8% agarose gel and transferred to a nylon membrane. Membranes were baked at 80° C. for 2 hours and prehybridized at 65° C. for 2 hours in 10 ml, 250 mM NaHPO$_4$.H$_2$O, 250 mM Na$_2$HPO$_4$-7H$_2$O, 7% sodium dodecyl sulfate (SDS), 1% BSA, and 1 mM EDTA.

$^{32}$P-Labeled IGF-I receptor cDNA (Boehringer Mannheim, Indianapolis, IN) with a specific activity of 6×10$^7$ dpm was prepared by random priming. Hybridization was carried out at 65° C. for 24 hours. Membrane was washed twice for 15 minutes in 200 ml, 2×SSC (20×SSC=3 M sodium chloride and 0.3 M sodium citrate) and 0.1% SDS at 65° C., followed by washing twice in 200 ml, 0.2×SSC-0.1 SDS for 15 min at 65° C. Filters were autoradiographed for 7 days at -70° C., using Kodak film (Eastman Kodak, Rochester, N.Y.) and intensifying screens.

The human receptor probe hybridized appropriately to all transfectant DNA samples but only hybridized minimally to DNA extracted from untransfected GC cells and Rat I fibroblasts, confirming that the exogenous human IGF-I receptor cDNAs were integrated into genomic DNA of these cells. The major ~5 kilobase DNA fragment which was expected to be released from pRSV-IGFIR by digestion with EcoRI was visualized in each transfectant, in addition to randomly sized DNA bands.

EXAMPLE VI

Characterization of Variant IGF-I Receptor

Variant IGF-I receptor formation (endogenous rat IGF-I receptor subunit/variant human IGF-I receptor subunit and/or variant human IGF-I receptor subunit/variant human IGF-I receptor subunit) was demonstrated by metabolically labeling transfectants with translabeled $^{35}$S-methionine (ICN, Irvine, California) and then immunoprecipitating the proteins with both αIR3 (Oncogene, Manhesset, N.Y.) and Ab 1-2 monoclonal antibody obtained from Dr. K. Siddle, University of Cambridge, Cambridge, England.

Confluent GC cells and Rat I fibroblast cells transfected with WT IGF-I receptor cDNA and $^{952}$STOP IGF-I receptor cDNA cells were rinsed with 5 ml phosphate-buffered saline (PBS) and metabolically labeled at 37° C. with 0.5 mCi [$^{35}$S] methionine (CSA, 1,049 ci/mmol) in 5 ml serum-free methionine-free medium. After 16 hours, the cells were lysed with lysis buffer (0.01 M NaCl, 0.5% deoxycholate, 1% Triton X-100, 0.1% SDS, 0.0% sodium azide, and 1 mM phenylmethylsulfonyl fluoride) and centrifuged at 3,000 rpm for 15 minutes at 4° C. Either αIR3 or Ab 1-2 were used at 1:500 or a 1:300 final concentration, respectively. Immune complexes were precipitated with protein A-Sepharose (Pharmacia Inc., Piscataway, N.J.). The pellets were then washed and loaded onto 4% nondenaturing polyacrylamide SDS gels along with prestaining protein molecular weight markers (Bethesda Research Laboratories, Gaitherburg, Md.).

IR3 recognizes the alpha subunit of human IGF-I receptor. Thus, the 460-kD WT receptor holotetramer and the truncated 300-kD $^{952}$STOP variant receptor holotetramer appear as distinct bands on the gel in response to immunoprecipitation with IR3. Ab 1-2 recognizes a carboxy terminal beta-subunit epitope of both rat and human IGF-I receptor, and therefore identifies the 360 kD variant (rat IGF-I receptor subunit/variant human IGF-I receptor subunit) receptor heterotetramer as a distinct band on the gel.

The intact human IGF-I receptor holotetramer was immunoprecipitated by both IR3 and Ab 1-2 in WT transfectants. IR3 precipitated the variant truncated-human receptor holotetramer in $^{952}$STOP transfectants. The only predominant band in response to immunoprecipitation of $^{952}$STOP transfectants with Ab 1-2 was the 360 kD variant rat/human hybrid receptor.

EXAMPLE VII

Longevity of Variant IGF-I Receptors

To study the IGF-I receptor biosynthetic half-life, semiconfluent GC cell transfectants were metabolically labeled with [$^3$S] methionine as in Example VI. After 16 hours, medium was replenished with serum-free defined (SFD) medium containing methionine with or without 6.5 nM IGF-I. After further incubation at 37° C., the cells were harvested at 0, 0.5, 2, 6 and 16 hours and processed as described in Example VI.

Half-life of WT receptors was greater than 6 hours. Densitometric scanning revealed a 90% increase in receptor degradation by 16 hours. The addition of ligand appeared not to have influenced the rate of degradation of the receptors. In $^{952}$STOP transfectants, variant rat/human hybrid receptor degradation rates were clearly slower, and by 16 hours the majority of synthesized receptors were still present. Similarly, the presence of ligand did not affect the variant rat/human hybrid receptor half-life. Variant truncated-human IGF-I holotetramers also appeared to degrade at a slower rate, similar to the slow degradation of variant rat/human hybrid receptors.

EXAMPLE VIII

IGF-I Internalization

About 1×10$^6$ Rat I fibroblast and GC cell transfectants were incubated with [$^{125}$I] IGF-I (40–50,000 cpm) in 0.5 ml DMEM (pH 7.8) containing 1% bovine serum albumin and 10 mM HEPES for 30 minutes at 37° C. At the end of the indicated incubation period, the medium was acidified by addition of 30 μl 1N HCl and allowed to incubate at 4° C. for an additional 6 minutes. Intracellular (acid-resistant) or cell-associated [$^{125}$I] IGF-I was determined as described in Example VI. Degraded [$^{125}$I] IGF-I was assessed by trichloroacetic acid precipitation (10%) of 300 μl of incubation buffer. After 4 more minutes at 4° C., the degraded [$^{125}$I] IGF-I in the supernatant was determined by gamma counting as described in Levy J. R., et al. *Endocrinology*, 119:572–579 (1986). Percent internalization is calculated by the following equation:

$$\frac{\text{intracellular} + \text{degraded}}{\text{surface} + \text{intracellular} + \text{degraded}} \times 100$$

after subtraction of respective values for untransfected cells.

GC cells transfected with cDNA having amino acid substitutions at positions 940, 943 or 950 and IGFIR-CRH transfectants, as well as the WT transfectants, internalized 46–70% of exogenous [$^{125}$I] IGF-I. In contrast, the $^{957}$Ala transfectant only internalized 24% total bound [$^{125}$I] IGF-I and the ΔA22 and the $^{1003}$Ala transfectants failed to internalize labeled IGF-I ligand.

Similarly, both untransfected Rat 1 fibroblasts and WT transfectants internalized [$^{125}$I] IGF-I in a time dependent manner. However, $^{952}$STOP transfectants failed to internalize labeled ligand during a 30 minute incubation period.

These internalization studies, considered in light of the results of the immunoprecitation assays of Example VI, reveal that the variant IGF-I receptor subunits produced from amino acid substitutions at residue 957 and 1003 and deletion mutations, complex with endogenous IGF-I receptor subunits of the Rat I fibroblast and GC cells, forming variant rat/human hybrid IGF-I receptors. These variant IGF-I receptors exert a negative trans-dominant effect on endogenous IGF-I receptor ligand internalization.

EXAMPLE IX

Variant IGF-I Receptor Autophosphorylation and Phosphorylation of Endogenous Substrate Transfectant GC cells labeled for 10 or 16 hours with [$^{35}$S] methionine were washed with PBS and incubated with or without IGF-I (6.5 nM) in serum-free defined medium for 1 minute at 37° C. Cells were then lysed with lysis buffer (1% Triton X-100, 30 mM sodium pyrophosphate, 10 mM Tris (pH 7.6), 5 mM EDTA (pH 8), 50 mM NaCl, 0.1% bovine serum albumin, 2 mM sodium orthovanadate, 200 mM phenylmethylsulfonyl fluoride) and centrifuged for 15 minutes at 3000 rpm.

Immunoprecipitation was performed using a monoclonal anti-phosphotyrosine antibody, either Ab 2 or PY 20, at 4° C. for 3 or 16 hours, respectively. (Ab 2 obtained from Oncogene Science, Manhasset, N.Y. PY 20 obtained from ICN, Costa Mesa, Calif.) Protein A-Sepharose with anti-mouse IgG (Sigma Chemical Corp., St. Louis, Mo.) for assays performed with Ab 1-2 and without anti-mouse IgG for assays performed with PY 20 was incubated with the monoclonal anti-phosphotyrosine antibody cell lysate complex for 2 hours at room temperature. Immunoprecipitates were washed six times in 0.9 ml lysis buffer, resuspended in 0.04 ml sample buffer, heated to 95° C. for 3–5 minutes, and electrophoresed on 7.5% sodium dodecyl sulfate-polyacrylamide gels.

In response to IGF-I ligand, WT and $^{957}$Ala transfectants induced tyrosine phosphorylation of both the beta subunit of the IGF-I receptor (97kD) and cytoplasmic protein substrates containing tyrosine residues, pp185 and/or IRS-1 (165–185 kD). The $^{950}$Ala transfectants failed to phosphorylate IRS-1 but otherwise demonstrated similar phosphorylation to the WT transfectants, albeit of lesser intensity. The $^{943}$Ala transfectants autophosphorylated the beta subunit of the receptor but the phosphorylation of IRS-1 was reduced as compared to WT transfectants. The $^{1003}$Ala and $^{952}$STOP transfectants failed to undergo ligand-mediated IGF-I receptor autophosphorylation and endogenous protein phosphorylation.

These results suggest that the tyrosine residues at positions 950 and possibly 943 are important sites for IRS-1 phosphorylation, and that IRS-1 may mediate IGF-I ligand signaling to the growth hormone gene. Moreover, the level of growth hormone suppression approximately parallels the IGF-I stimulated tyrosine kinase activity in cells as assessed by tyrosine phosphorylation of the IGF-I receptor substrate, IRS-1. The lysine residue at position 1003 in the ATP domain is critical for autophosphorylation and phosphorylation.

EXAMPLE X

Variant IGF-I Receptors Inhibit IGF-I Signaling

To determine the effect of variant IGF-I receptor formation on endogenous rat IGF-I receptor ability to transduce the IGF-I signal to the growth hormone gene, approximately 5×10$^5$ GC cells were plated on 9-cm$^2$ multiwells and grown for 24 hours in growth medium. The medium was then aspirated and replenished with 1.5–2.0 ml Yamasaki, H., et al., *Endocrinology*, 128: 857–862 (1991) (0.6 nM triiodothyronine (T$_3$), 0.2 ng/ml parathyroid hormone (PTH), 10 mg/ml transferrin, 0.1 ng/ml epidermal growth factor, 0.2 mg/nl fibroblast growth factor, 10 pg/ml glucagon, 100 nM hydrocortisone, and 0.3% bovine serum albumin in DMEM) with or without 6.5 nM IGF-I. Aliquots of medium were removed at various time intervals and assayed for rat growth hormone using radiolabeled rat growth hormone and anti-rat growth hormone antibody supplied by the National Hormone and Pituitary Program, National Institute of Diabetes and Digestive and Kidney Diseases (Bethesda, Md.). Percent growth hormone secretion suppression was calculated by the following formula:

(GH secreted from UC–GH secreted from TC)/GH secreted from UC×100 where GH is growth hormone, UC is untreated cells and TC is treated cells.

After 18 hours of IGF-I treatment, untransfected cells only suppressed growth hormone by 20%, whereas WT transfectants already exhibited a 58% suppression of growth hormone secretion. Both the $^{940}$Ala and $^{957}$Ala point mutations showed enhanced IGF-I suppression of growth hormone, similar to that observed in the WT transfectants. The $^{943}$Ala point mutation showed a suppressive effect intermediate between IGF-I action in WT and untransfected cells. The transfectants with amino acid substitutions at residue 950 or 1003 responded to IGF-I similarly to untransfected cells. The $^{952}$STOP failed to suppress growth hormone secretion.

By 36 hours, untransfected cells showed a 40% suppression of growth hormone, and WT transfectants a 60% suppression of growth hormone. However, $^{952}$STOP cells still failed to respond to the IGF-I ligand and in fact, growth hormone secretion was higher in these cells than in non-transfected control cells despite the presence of endogenous IGF-I receptors. The $^{952}$STOP transfectants were therefore completely devoid of biological signaling to growth hormone despite the presence of endogenous rat IGF-I receptors.

These observations suggest that of the three tyrosine residues localized in the juxta-membrane domain of the human IGF-I receptor, the tyrosine residue at position 950 is critical for the IGF-I signaling to the growth hormone gene, while the tyrosine at position 957 does not appear to be required. The reduced efficiency with which the $^{943}$Ala suppressed growth hormone in response to IGF-I suggests the possibility that the tyrosine at position 943 may be an important folding and/or contact point for protein(s) involved in the signaling cascade to the growth hormone gene in the somatotroph nucleus. Clearly, the $^{952}$STOP IGF-I receptor subunit behaves as a dominant negative inhibitor of endogenous IGF-I receptor function.

EXAMPLE XI

Variant IGF-I Receptors Modify IGF-I Mediated Cell Proliferation

To further demonstrate that variant IGF-I receptor formation modifies endogenous receptor function, cellular proliferation in the presence and absence of IGF-I was studied by seeding about 1×10⁴ Rat I fibroblast WT and $^{952}$STOP transfectants in SFD medium for 24 hrs. Medium was then replenished and a concentration of 3.25 nM IGF-I was added to the "IGF-I Present" test wells. After 72 hours incubation, medium was aspirated and the monolayer washed twice with 5 ml PBS (pH 7.4).

100 µl of crystal violet (Sigma Chemical Co., St. Louis, Mo.) made up to 0.5% in methanol at room temperature was added to each well for 15 minutes. The wells were then destained with 1 ml H$_2$O and allowed to air dry. The crystals were then dissolved in 100 µl 0.1 M sodium citrate (pH 4.2) and 50% ethanol for 30 minutes at room temperature. Plates were read on Elisa plate reader at 540 nM wavelength. Growth stimulatory ratios (% GSR) were calculated as follows:

$$\% \ GSR = \frac{A_{sample} - A_{blank}}{A_{control} - A_{blank}} \times 100$$

Where A=absorbance. Data were corrected for mock transfected cells (I51Neo) by subtracting out the I51Neo values.

Table 1 provides the growth stimulatory ratio for WT and $^{952}$STOP transfectants in the presence and absence of IGF-I, measured as a percent of cell proliferation of control transfected cells.

TABLE 1

Growth Stimulatory Ratio

| Transfectant | IGF-I Absent | IGF-I Present (3.25 nM) |
|---|---|---|
| WT | 100 ± 10 | 300 ± 20 |
| $^{952}$STOP | *70 ± 5 | *80 ± 1 |

*p < 0.005 WT vs. $^{952}$STOP transfectants.
WT transfectants grew faster than $^{952}$STOP transfectants (p < 0.005) both in the absence and presence of IGF-I ligand. $^{952}$STOP transfectants did not respond to IGF-I.

EXAMPLE XII

Variant IGF-I Receptors Modify IGF-I Mediated DNA Synthesis

The blunted growth response of the variant IGF-I receptor transfectants identified in Example XII was confirmed by measuring DNA synthesis by [³H] thymidine uptake after IGF-I treatment.

About 1×10⁴ Rat I fibroblast, WT or $^{952}$STOP transfectants were grown in SFD medium for 24 hours. Medium was then replenished and 2 ml concentration of 3.25 nM IGF-I was added to the "IGF-I Present" test wells. After 48 hours incubation, [³H] thymidine (1 µCi) (ICN Biochemicals, Costa Mesa, Calif.) was added to the medium and the cells were allowed to incubate at 37° C. for 5 hours. Medium was then aspirated and 100 µl of cold tricarboxylic acid (10%) was added to each well for 20 minutes at 4° C. Following aspiration the wells were washed twice with 10% tricarboxylic acid. 100 µl of 1N sodium hydroxide was then added to each well and the plates incubated on a shaker for 15–30 minutes at room temperatures. Following solubilization, 90 µl was removed from each well for counting in a liquid scintillation counter. The results were corrected by subtracting values for control transfected I51Neo cells. The values presented in Table 2 represent the mean of six determinations.

TABLE 2

[³H]Thymidine Incorporation Into Transfectants

| Transfectant | IGF-I Absent | IGF-I Present (3.25 nM) |
|---|---|---|
| WT | 165 ± 6 | **323 ± 9 |
| $^{952}$STOP | *57 ± 2.7 | *55 ± 2.4 |

*p < 0.005, WT vs. $^{952}$STOP.
**p < 0.005, IGF-I vs. no IGF-I.

[³H] thymidine incorporation into WT transfectants more than doubled in the presence of IGF-I. IGF-I, however, did not stimulate DNA synthesis in $^{952}$STOP transfectants. Furthermore, the absolute growth rate of $^{952}$STOP transfectants was markedly lower than that of WT or untransfected Rat 1 fibroblasts. These results demonstrate that IGF-I is a positive growth regulator operating through intact endogenous IGF-I receptors of Rat I fibroblasts and that overexpression of variant IGF-I receptor cDNA can be used to modify this positive growth regulation.

EXAMPLE XIII

Variant IGF-I Receptors Alter Cell Morphology and Inhibit Colony Formation

About 1×10⁵ untranfected Rat I fibroblasts, WT transfectants or $^{952}$STOP transfectants were each plated in SFD medium. A concentration of 50 nM IGF-I or 650 nM insulin was added to test plates and all plates were allowed to incubate for 48 hours.

WT transfectants exhibited a marked change in cell morphology after treatment with either IGF-I or insulin. Transfectants grown in the absence of ligand had a normal phenotypic appearance similar to that of untransfected Rat 1 fibroblasts and $^{952}$STOP transfectants. In the presence of IGF-I or insulin, however, WT transfectants rounded up and became loosely adherent to the plate. Neither the untransfected Rat 1 fibroblast nor the $^{952}$STOP transfectants exhibited a significant change in cellular morphology following ligand addition.

IGF-I is >10-fold more potent than insulin in promoting this altered morphology and exhibits 10 times the affinity for binding IGF-I receptor than insulin. These observations indicate that these growth factor mediated phenotypic changes occur through the overexpressed IGF-I receptor which can be modified by the presence of variant IGF-I receptor.

To determine whether changes in colony morphology implied a more universal change in the growth phenotype of transfectants, their growth in soft agar was analyzed. About 2×10³ untransfected Rat I fibroblast, WT transfectants or $^{952}$STOP transfectants were plated in groups of 6 in 35 mm 0.3% soft agar containing 0.42 ml, 0.3% Bacto-Agar, 0.83 ml αMEM, 0.33 ml, 10% fetal calf serum, 0.2 ml penicillin and streptomycin combined, in the absence or presence of 13 nM IGF-I. Plates were incubated at 37° C. for 12 days. All colonies containing >40 cells were scored. The figures in Table 3 represent the mean number of colonies counted in six wells.

TABLE 3

Colony Formation in Soft Agar

| Transfectant | IGF-I Absent | IGF-I Present (13 nM) |
|---|---|---|
| Untransfected | 21.8 ± 5.3 | 37.5 ± 7.5 |
| WT | *46.2 ± 9.1 | *65.5 ± 3.4 |
| $^{952}$STOP | 0.7 | 1.8 |

*p < 0.001, vs. untransfected Rat I fibroblast.

Untransfected Rat 1 fibroblast grew in soft agar, but their colony size was much smaller than that of WT transfectants. The small untransfected Rat 1 fibroblast colonies increased in size and number in response to IGF-I, but were still fewer and smaller in size than the WT colonies in the absence of IGF-I. After ligand treatment, WT colonies increased both in size and number. In contrast, $^{952}$STOP transfectants failed to grow in soft agar in the absence of ligand and showed only minimal growth in the presence of ligand.

Thus, the endogenous rat IGF-I receptors were unable to promote anchorage-independent growth of $^{952}$STOP transfectants, suggesting that expression of variant IGF-I subunits results in the formation of non-functional variant receptors.

EXAMPLE XIV

Variant IGF-I Receptors Inhibit In Vivo Tumorigenicity

To determine if variant receptors exerted a dominant-negative phenotypic effect in vivo, three groups of nine athymic nude mice were injected subcutaneously over the right or left flank with about 1×10$^6$ untransfected Rat I fibroblasts, WT transfectants or $^{952}$STOP transfectants. Mice were observed for eight weeks prior to sacrifice.

All the mice injected with WT transfectants developed palpable and visible tumors within three weeks of injection. Six of nine mice injected with untransfected Rat 1 fibroblasts developed tumors only after 5–6 weeks. Mice injected with WT transfectants developed large tumors as compared to those in mice injected with untransfected Rat 1 fibroblasts which were smaller and necrotic. None of the mice injected with $^{952}$STOP transfectants developed tumors during the 8 week monitoring period.

Following sacrifice, solid tumors resulting from Rat 1 fibroblast (Rat I MT) and WT transfectants (WT MT1–9) were enzymatically dispersed with collagenase (0.35%) and hyaluronidase (0.1%) and cultured in vitro in G418. Both native as well as ex viva Rat I MT cells failed to grow in the presence of genticin. However, all the WT MT1–9 cells derived ex vivo proliferated in vitro in G418 at 600 μg/ml.

Specific [$^{125}$I]-IGF-I binding to these cells, performed as described in Example IV, demonstrated that the ex vivo WT MT1–9 cells continued to overexpress IGF-I receptors (20–41% specific IGF-I binding), as compared to untransfected Rat I fibroblasts or Rat I MT cells (5% specific IGF-I binding).

Southern blot analysis carried out as described in Example V on EcoR1 digested DNA from Rat I MT and WT M1–9 tumor derived cells, confirmed that the variant IGF-I receptor was still integrated into the ex vivo cells.

Pathological examination of the WT M4 and Rat I MT formalin fixed tumors revealed that the tumors contained vimentin immunoreactivity consistent with sarcoma differentiation. They did not express keratin, S100 protein, neurofilaments, leukocyte common antigen, desmin or myoglobin, thus excluding carcinomas, neural differentiation, lymphoma or muscle differentiation. Electron microscopy was consistent with sarcomatous differentiation. Both tumors were fibrosarcomas, with the Rat I MT tumors having large areas of necrosis consistent with the more friable nature of this tumor, compared to the Rat WT M4 tumor which was extremely hard, and had few areas of necrosis.

Although the invention has been described with reference to presently preferred embodiments, it should be understood that various modifications can be made without departing from the spirit of the invention.

We claim:

1. A recombinant polynucleic acid encoding a variant beta subunit of a mammalian IGF-I receptor, comprising
   an IGF-I receptor alpha subunit binding region,
   a transmembrane region, and
   a juxta-membrane region comprising residues 930 through 972 of SEQ ID NO: 2, wherein at least one amino acid of the juxtamembrane region, other than amino acid 950, is deleted or replaced with one or more amino acid(s) which does (do) not occur at the corresponding residue of SEQ ID NO: 2 wherein the variant beta subunit binds endogenous or variant IGF-I receptor subunits, and when an IGF-I receptor comprises the variant IGF-I beta subunit, the variant IGF-I receptor displays a dominant negative effect relative to the endogenous receptor when present in a target cell, in at least one IGF-I mediated function selected from the group consisting of tyrosine kinase activity, ligand binding, ATP binding, cell differentiation, IGF-I receptor degradation, ligand internalization, autophosphorylation, cytoplasmic substrate phosphorylation, cytoplasmic substrate binding, growth hormone secretion suppression, DNA synthesis, cell proliferation, cell transformation, and cell tumorigenesis.

2. The recombinant polynucleic acid of claim 1, wherein the IGF-I receptor alpha subunit binding region comprises residues 744 through 906 of SEQ ID NO: 2.

3. The recombinant polynucleic acid of claim 1, wherein the transmembrane region comprises residues 907 through 929 of SEQ ID NO: 2.

4. The recombinant polynucleic acid of claim 3, wherein the IGF-I receptor alpha subunit binding region comprises residues 744 through 906 of SEQ ID NO: 2.

5. The recombinant polynucleic acid of claim 4, further comprising a polynucleotide encoding residues 711 through 743 of SEQ ID NO: 2.

6. The recombinant polynucleic acid of claim 5, further comprising a polynucleotide encoding an alpha subunit of a mammalian IGF-I receptor.

7. The recombinant polynucleic acid of claim 1, wherein the IGF-I receptor displays a dominant negative effect in IGF-I receptor-mediated, receptor degradation with respect to that of the endogenous IGF-I receptor.

8. The recombinant polynucleic acid of claim 1, wherein the IGF-I receptor comprising the variant beta subunit displays a dominant negative effect in IGF-I receptor-mediated, ligand internalization with respect to that of the endogenous IGF-I receptor.

9. The recombinant polynucleic acid of claim 1, wherein the IGF-I receptor comprising the variant beta subunit displays a dominant negative effect in IGF-I receptor-mediated, autophosphorylation with respect to that of the endogenous IGF-I receptor.

10. The recombinant polynucleic acid of claim 1, wherein the IGF-I receptor comprising the variant beta subunit displays a dominant negative effect in IGF-I receptor-mediated, cytoplasmic substrate phosphorylation with respect to that of the endogenous IGF-I receptor.

11. The recombinant polynucleic acid of claim 1, wherein the IGF-I receptor comprising the variant beta subunit displays a dominant negative effect in IGF-I receptor-mediated, cytoplasmic substrate binding with respect to that of the endogenous IGF-I receptor.

12. The recombinant polynucleic acid of claim 1, wherein the IGF-I receptor comprising the variant beta subunit displays a dominant negative effect in IGF-I receptor-mediated, growth hormone secretion suppression with respect to that of the endogenous IGF-I receptor.

13. The recombinant polynucleic acid of claim 1, wherein the IGF-I receptor comprising the variant beta subunit displays a dominant negative effect in IGF-I receptor-mediated, DNA synthesis with respect to that of the endogenous IGF-I receptor.

14. The recombinant polynucleic acid of claim 1, wherein the IGF-I receptor comprising the variant beta subunit displays a dominant negative effect in IGF-I receptor-mediated, cell proliferation with respect to that of the endogenous IGF-I receptor.

15. The recombinant polynucleic acid of claim 1, wherein the IGF-I receptor comprising the variant beta subunit displays a dominant negative effect in IGF-I receptor-mediated, cell transformation with respect to that of the endogenous IGF-I receptor.

16. The recombinant polynucleic acid of claim 1, wherein the IGF-I receptor comprising the variant beta subunit displays a dominant negative effect in IGF-I receptor-mediated, cell tumorigenesis with respect to that of the endogenous IGF-I receptor.

17. The recombinant polynucleic acid of claim 1, wherein the IGF-I receptor comprising the variant beta subunit displays a dominant negative effect in IGF-I receptor-mediated tyrosine kinase activity with respect to that of the endogenous IGF-I receptor.

18. The recombinant polynucleic acid of claim 1, wherein the IGF-I receptor comprising the variant beta subunit displays a dominant negative effect in IGF-I receptor-mediated ligand binding activity with respect to that of the endogenous IGF-I receptor.

19. The recombinant polynucleic acid of claim 1, wherein the IGF-I receptor comprising the variant beta subunit displays a dominant negative effect in IGF-I receptor-mediated ATP binding activity with respect to that of the endogenous IGF-I receptor.

20. The recombinant polynucleic acid of claim 1, encoding an amino acid other than tyrosine at position 943 of SEQ ID NO: 2.

21. The recombinant polynucleic acid of claim 20, encoding amino acid alanine at position 943 of SEQ ID NO: 2.

22. The recombinant polynucleic acid of claim 21, wherein the IGF-I receptor-mediated function is selected from the group consisting of tyrosine kinase activity, autophosphorylation, phosphorylation of cytoplasmic substrate and growth hormone secretion suppression.

23. The recombinant polynucleic acid of claim 1, encoding an amino acid other than tyrosine at position 957 of SEQ ID NO: 2.

24. The recombinant polynucleic acid of claim 23, encoding an alanine at position 957 of SEQ ID NO: 2.

25. The recombinant polynucleic acid of claim 24 wherein the IGF-I receptor comprising the variant beta subunit displays a dominant negative effect in IGF-I mediated ligand-internalization.

26. The recombinant polynucleic acid of claim 1, wherein the IGF-I receptor comprising the variant beta subunit displays a dominant negative effect in an IGF-I receptor-mediated function selected from the group consisting of IGF-I receptor degradation, ligand internalization, cell colony formation, DNA synthesis, cell proliferation, cell transformation, and cell tumorigenesis.

27. A vector comprising the polynucleic acid of claim 1.

28. A cell comprising the vector of claim 27.

29. A method of making a modified recombinant polynucleic acid encoding subunits of a functional IGF-I receptor comprising at least one modified beta subunit, comprising subcloning a further polynucleic acid encoding at least one alpha subunit of a mammalian IGF-I receptor into the vector of claim 27; and recovering the modified polynucleic acid.

30. The method of claim 29, further comprising prior to the recovering step transfecting the cloned vector into a host cell;

culturing the transfected host cell under conditions effective for multiplying the vector carrying the modified polynucleic acid; and allowing the vector comprising the modified polynucleic acid to accumulate; and isolating the vector containing the modified polynucleic acid.

31. A method of making an IGF-I receptor comprising at least one modified beta subunit, comprising subcloning a further polynucleic acid encoding at least one alpha subunit of the mammalian IGF-I receptor into the vector of claim 27;

transfecting a host cell with the vector;

culturing the transfected host cell under conditions effective for expressing the IGF-I receptor comprising at least one modified IGF-I beta subunit;

allowing the IGF-I receptor to accumulate; and isolating the receptor.

32. A cell comprising the polynucleic acid of claim 1.

33. The recombinant polynucleic acid of claim 1, encoding an amino acid other than glycine at position 940 of SEQ ID NO: 2.

34. The polynucleic acid of claim 33, encoding an alanine at position 957 of SEQ ID NO: 2.

35. The polynucleic acid of claim 34, wherein the IGF-I receptor comprising the variant beta subunit displays a dominant negative effect in IGF-I receptor-mediated, ligand-internalization with respect to that of the endogenous IGF-I receptor.

36. The polynucleic acid of claim 1, wherein the nucleotides encoding amino acids 943 through 966 of SEQ ID NO: 2 of the juxta-membrane region are deleted.

37. The polynucleic acid of claim 36, wherein the IGF-I receptor comprising the variant IGF-I beta subunit displays a dominant negative effect in IGF-I mediated, ligand-internalization with respect to that of the endogenous IGF-I receptor.

38. The polynucleic acid of claim 37, wherein the IGF-I receptor comprising the variant beta subunit displays a dominant negative effect in tyrosine kinase activity with respect to that of the endogenous IGF-I receptor.

39. The polynuclcic acid of claim 1, further comprising a polynucleotide encoding a variant beta IGF-I subunit, wherein at least one amino acid selected from the group consisting of amino acids present at positions 1003, 1131, 1135, 1136 and 1337 of SEQ ID NO:2.

40. The polynucleic acid of claim 37, wherein the IGF-I receptor comprising the variant beta subunit displays a dominant negative effect in tyrosine kinase activity with respect to that of the endogenous IGF-I receptor.

41. The recombinant polynucleic acid of claim 1, further comprising a polynucleotide encoding an alpha subunit of a mammalian IGF-I receptor.

42. A method of making a modified polynucleic acid encoding a modified, mammalian IGF-I receptor beta subunit, comprising obtaining a polynucleic acid encoding a beta subunit of an endogenous mammalian IGF-I receptor displaying a function selected from the group consisting of tyrosine kinase activity, ligand binding, ATP binding, cell differentiation, IGF-I receptor degradation, ligand internalization, autophosphorylation, phosphorylation of cytoplasmic substrate, binding of cytoplasmic substrate, growth hormone suppression, DNA synthesis, cell proliferation, cell transformation, and cell tumorigenesis, wherein the beta subunit comprises an alpha subunit binding region, a transmembrane region, and a juxta-membrane region comprising amino acid residues 930 to 972 of SEQ ID NO: 2;

modifying said polynucleic acid to produce a modified polynucleic acid encoding a modified IGF-I receptor beta subunit by deleting or replacing nucleotides encoding at least one amino acid at a position of the juxta-membrane region of the endogenous IGF-I receptor beta subunit, other than position 950, with one or more amino acid(s) that does (do) not occur at the corresponding position wherein the variant beta subunit when subsequently expressed binds to other endogenous IGF-I or variant receptor subunits to form a modified IGF-I receptor exhibiting at least one IGF-I receptor-mediated function in a dominant negative manner relative to the endogenous IGF-I receptor; and isolating the modified polynucleic acid.

43. The method of claim 42, further comprising cloning the modified polynucleic acid into a vector;

transfecting a host cell with the vector;

culturing the transfected host cell under conditions effective for multiplying the vector carrying the modified polynucleic acid;

allowing the vector carrying the modified polynucleic acid to accumulate; and isolating the vector comprising the modified polynucleic acid.

44. The method of claim 43, further comprising separating the modified polynucleic acid from the vector and isolating the modified polynucleic acid.

45. The method of claim 42, wherein the nucleotides encoding amino acid residue 943 of SEQ ID NO: 2 are modified to yield a different amino acid from that present in SEQ ID NO: 2.

46. The method of claim 42, wherein the nucleotides encoding amino acid residue 957 of SEQ ID NO: 2 are modified to yield a different amino acid from that present in SEQ ID NO: 2.

47. A method of making a modified, mammalian IGF-I receptor beta subunit, comprising obtaining a polynucleic acid encoding a beta subunit of an endogenous, mammalian IGF-I receptor displaying a function selected from the group consisting of tyrosine kinase activity, ligand binding, ATP binding, cell differentiation, IGF-I receptor degradation, ligand internalization, autophosphorylation, phosphorylation of cytoplasmic substrate, binding of cytoplasmic substrate, growth hormone suppression, DNA synthesis, cell proliferation, cell transformation and cell tumorigenesis, wherein the beta subunit comprises an alpha subunit binding region, a transmembrane region and a juxta-membrane region comprising amino acid residues 930 to 972 of SEQ ID NO: 2;

modifying the polynucleic acid encoding at least the juxta-membrane region to produce a modified polynucleic acid encoding a modified IGF-I receptor beta subunit by deleting or replacing a nucleotides encoding at least one amino acid at a position of the juxta-membrane region of the endogenous IGF-I receptor beta subunit, other than 950, with one or more amino acid(s) that does (do) not occur at the corresponding position, wherein the variant beta subunit when subsequently expressed binds to endogenous or variant IGF-1 receptor subunits to form a modified IGF-I receptor exhibiting at least one IGF-I receptor-mediated function in a dominant negative manner relative to the endogenous IGF-I receptor;

cloning the modified polynucleic acid into an expression vector;

transfecting the vector into a host cell;

culturing the transfected host cell under conditions effective for expressing the modified beta receptor subunit;

allowing the modified IGF-I beta receptor subunit to accumulate; and isolating the modified IGF-I beta receptor subunit.

48. The method of claim 47, wherein the polynucleic acid further encodes at least one alpha subunit of the IGF-I receptor.

49. The method of claim 47, wherein the nucleotides encoding amino acid residue 943 of SEQ ID NO: 2 are modified to yield a different amino acid from that present in SEQ ID No: 2.

50. The method of claim 47, wherein the nucleotides encoding amino acid residue 957 of SEQ ID NO: 2 are modified to yield a different amino acid from that present in SEQ ID NO: 2.

51. The method of claim 47, wherein the polynucleic acid encoding a modified beta subunit of a mammalian IGF-I receptor is produced by a truncation at the nucleotides encoding positions 943 to 966 of the juxta-membrane region.

52. The method of claim 51, wherein the vector further comprises a polynucleic acid encoding an endogenous beta subunit of the IGF-I receptor.

53. A recombinant polynucleic acid encoding a variant beta subunit of a mammalian IGF-I receptor, comprising an IGF-I receptor alpha subunit binding region, a transmembrane region, and a juxtamembrane region, wherein said polynucleic acid is modified to encode an amino acid other than lysine at position 1003 of SEQ ID NO: 2 and wherein the variant IGF-I receptor displays a dominant negative effect relative to the endogenous receptor.

54. The recombinant polynucleic acid of claim 53 encoding an alanine at position 1003 of SEQ ID NO: 2.

55. A recombinant polynucleic acid encoding a variant beta subunit of a mammalian IGF-I receptor, comprising an IGF-I receptor alpha subunit binding region, a transmembrane region, a juxtamembrane region, and a cytosolic tyrosine kinase domain, wherein said cytosolic tyrosine kinase domain is modified by deleting or replacing one or more amino acid(s) selected from the group consisting of residues 1131, 1135, 1136 and 1337 with an amino acid(s) that does (do) not occur at the corresponding position of SEQ ID NO: 2, wherein the variant beta subunit binds endogenous or variant IGF-I receptor subunits, and when an IGF-I receptor comprises the variant IGF-I beta subunit, the variant IGF-I receptor displays a dominant negative effect in cytosolic tyrosine kinase activity with respect to that of the endogenous receptor.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 4975 base pairs
      (B) TYPE: nucleic acid
      (C) STRANDEDNESS: double
      (D) TOPOLOGY: both (ii) MOLECULE TYPE: cDNA (xi) SEQUENCE DESCRIPTION: SEQ ID NO:1:

```
GAGAAAGGGA ATTTCATCCC AAATAAAAGG A ATG AAG TCT GGC TCC GGA GAA      52

GGG TCC CCG ACC TCG CTG TGG GGG CTC CTG TTT CTC TCC GCC GCG CTC    100

TCG CTC TGG CCG ACG AGT GGA GAA ATC TGC GGG CCA GGC ATC GAC ATC    148

CGC AAC GAC TAT CAG CAG CTG AAG CGC CTG GAG AAC TGC ACG GTG ATC    196
```

```
GAG GGC TAC CTC CAC ATC CTG CTC ATC TCC AAG GCC GAG GAC TAC CGC      244
AGC TAC CGC TTC CCC AAG CTC ACG GTC ATT ACC GAG TAC TTG CTG CTG      292
TTC CGA GTG GCT GGC CTC GAG AGC CTC GGA GAC CTC TTC CCC AAC CTC      340
ACG GTC ATC CGC GGC TGG AAA CTC TTC TAC AAC TAC GCC CTG GTC ATC      388
TTC GAG ATG ACC AAT CTC AAG GAT ATT GGG CTT TAC AAC CTG AGG AAC      436
ATT ACT CGG GGG GCC ATC AGG ATT GAG AAA AAT GCT GAC CTC TGT TAC      484
CTC TCC ACT GTG GAC TGG TCC CTG ATC CTG GAT GCG GTG TCC AAT AAC      532
TAC ATT GTG GGG AAT AAG CCC CCA AAG GAA TGT GGG GAC CTG TGT CCA      580
GGG ACC ATG GAG GAG AAG CCG ATG TGT GAG AAG ACC ACC ATC AAC AAT      628
GAG TAC AAC TAC CGC TGC TGG ACC ACA AAC CGC TGC CAG AAA ATG TGC      676
CCA AGC ACG TGT GGG AAG CGG GCG TGC ACC GAG AAC AAT GAG TGC TGC      724
CAC CCC GAG TGC CTG GGC AGC TGC AGC GCG CCT GAC AAC GAC ACG GCC      772
TGT GTA GCT TGC CGC CAC TAC TAC TAT GCC GGT GTC TGT GTG CCT GCC      820
TGC CCG CCC AAC ACC TAC AGG TTT GAG GGC TGG CGC TGT GTG GAC CGT      868
GAC TTC TGC GCC AAC ATC CTC AGC GCC GAG AGC AGC GAC TCC GAG GGG      916
TTT GTG ATC CAC GAC GGC GAG TGC ATG CAG GAG TGC CCC TCG GGC TTC      964
ATC CGC AAC GGC AGC CAG AGC ATG TAC TGC ATC CCT TGT GAA GGT CCT     1012
TGC CCG AAG GTC TGT GAG GAA GAA AAG AAA ACA AAG ACC ATT GAT TCT     1060
GTT ACT TCT GCT CAG ATG CTC CAA GGA TGC ACC ATC TTC AAG GGC AAT     1108
TTG CTC ATT AAC ATC CGA CGG GGG AAT AAC ATT GCT TCA GAG CTG GAG     1156
AAC TTC ATG GGG CTC ATC GAG GTG GTG ACG GGC TAC GTG AAG ATC CGC     1204
CAT TCT CAT GCC TTG GTC TCC TTG TCC TTC CTA AAA AAC CTT CGC CTC     1252
ATC CTA GGA GAG GAG CAG CTA GAA GGG AAT TAC TCC TTC TAC GTC CTC     1300
GAC AAC CAG AAC TTG CAG CAA CTG TGG GAC TGG GAC CAC CGC AAC CTG     1348
ACC ATC AAA GCA GGG AAA ATG TAC TTT GCT TTC AAT CCC AAA TTA TGT     1396
GTT TCC GAA ATT TAC CGC ATG GAG GAA GTG ACG GGG ACT AAA GGG CGC     1444
CAA AGC AAA GGG GAC ATA AAC ACC AGG AAC AAC GGG GAG AGA GCC TCC     1492
TGT GAA AGT GAC GTC CTG CAT TTC ACC TCC ACC ACC ACG TCG AAG AAT     1540
CGC ATC ATC ATA ACC TGG CAC CGG TAC CGG CCC CCT GAC TAC AGG GAT     1588
CTC ATC AGC TTC ACC GTT TAC TAC AAG GAA GCA CCC TTT AAG AAT GTC     1636
ACA GAG TAT GAT GGG CAG GAT GCC TGC GGC TCC AAC AGC TGG AAC ATG     1684
GTG GAC GTG GAC CTC CCG CCC AAC AAG GAC GTG GAG CCC GGC ATC TTA     1732
CTA CAT GGG CTG AAG CCC TGG ACT CAG TAC GCC GTT TAC GTC AAG GCT     1780
GTG ACC CTC ACC ATG GTG GAG AAC GAC CAT ATC CGT GGG GCC AAG AGT     1828
GAG ATC TTG TAC ATT CGC ACC AAT GCT TCA GTT CCT TCC ATT CCC TTG     1876
GAC GTT CTT TCA GCA TCG AAC TCC TCT TCT CAG TTA ATC GTG AAG TGG     1924
AAC CCT CCC TCT CTG CCC AAC GGC AAC CTG AGT TAC TAC ATT GTG CGC     1972
TGG CAG CGG CAG CCT CAG GAC GGC TAC CTT TAC CGG CAC AAT TAC TGC     2020
TCC AAA GAC AAA ATC CCC ATC AGG AAG TAT GCC GAC GGC ACC ATC GAC     2068
ATT GAG GAG GTC ACA GAG AAC CCC AAG ACT GAG GTG TGT GGT GGG GAG     2116
```

```
AAA GGG CCT TGC TGC GCC TGC CCC AAA ACT GAA GCC GAG AAG CAG GCC      2164

GAG AAG GAG GAG GCT GAA TAC CGC AAA GTC TTT GAG AAT TTC CTG CAC      2212

AAC TCC ATC TTC GTG CCC AGA CCT GAA AGG AAG CGG AGA GAT GTC ATG      2260

CAA GTG GCC AAC ACC ACC ATG TCC AGC CGA AGC AGG AAC ACC ACG GCC      2308

GCA GAC ACC TAC AAC ATC ACC GAC CCG GAA GAG CTG GAG ACA GAG TAC      2356

CCT TTC TTT GAG AGC AGA GTG GAT AAC AAG GAG AGA ACT GTC ATT TCT      2404

AAC CTT CGG CCT TTC ACA TTG TAC CGC ATC GAT ATC CAC AGC TGC AAC      2452

CAC GAG GCT GAG AAG CTG GGC TGC AGC GCC TCC AAC TTC GTC TTT GCA      2500

AGG ACT ATG CCC GCA GAA GGA GCA GAT GAC ATT CCT GGG CCA GTG ACC      2548

TGG GAG CCA AGG CCT GAA AAC TCC ATC TTT TTA AAG TGG CCG GAA CCT      2596

GAG AAT CCC AAT GGA TTG ATT CTA ATG TAT GAA ATA AAA TAC GGA TCA      2644

CAA GTT GAG GAT CAG CGA GAA TGT GTG TCC AGA CAG GAA TAC AGG AAG      2692

TAT GGA GGG GCC AAG CTA AAC CGG CTA AAC CCG GGA AAC TAC ACA GCC      2740

CGG ATT CAG GCC ACA TCT CTC TCT GGG AAT GGG TCG TGG ACA GAT CCT      2788

GTG TTC TTC TAT GTC CAG GCC AAA ACA GGA TAT GAA AAC TTC ATC CAT      2836

CTG ATC ATC GCT CTG CCC GTC GCT GTC CTG TTG ATC GTG GGA GGG TTG      2884

GTG ATT ATG CTG TAC GTC TTC CAT AGA AAG AGA AAT AAC AGC AGG CTG      2932

GGG AAT GGA GTG CTG TAT GCC TCT GTG AAC CCG GAG TAC TTC AGC GCT      2980

GCT GAT GTG TAC GTT CCT GAT GAG TGG GAG GTG GCT CGG GAG AAG ATC      3028

ACC ATG AGC CGG GAA CTT GGG CAG GGG TCG TTT GGG ATG GTC TAT GAA      3076

GGA GTT GCC AAG GGT GTG GTG AAA GAT GAA CCT GAA ACC AGA GTG GCC      3124

ATT AAA ACA GTG AAC GAG GCC GCA AGC ATG CGT GAG AGG ATT GAG TTT      3172

CTC AAC GAA GCT TCT GTG ATG AAG GAG TTC AAT TGT CAC CAT GTG GTG      3220

CGA TTG CTG GGT GTG GTG TCC CAA GGC CAG CCA ACA CTG GTC ATC ATG      3268

GAA CTG ATG ACA CGG GGC GAT CTC AAA AGT TAT CTC CGG TCT CTG AGG      3316

CCA GAA ATG GAG AAT AAT CCA GTC CTA GCA CCT CCA AGC CTG AGC AAG      3364

ATG ATT CAG ATG GCC GGA GAG ATT GCA GAC GGC ATG GCA TAC CTC AAC      3412

GCC AAT AAG TTC GTC CAC AGA GAC CTT GCT GCC CGG AAT TGC ATG GTA      3460

GCC GAA GAT TTC ACA GTC AAA ATC GGA GAT TTT GGT ATG ACG CGA GAT      3508

ATC TAT GAG ACA GAC TAT TAC CGG AAA GGA GGC AAA GGG CTG CTG CCC      3556

GTG CGC TGG ATG TCT CCT GAG TCC CTC AAG GAT GGA GTC TTC ACC ACT      3604

TAC TCG GAC GTC TGG TCC TTC GGG GTC GTC CTC TGG GAG ATC GCC ACA      3652

CTG GCC GAG CAG CCC TAC CAG GGC TTG TCC AAC GAG CAA GTC CTT CGC      3700

TTC GTC ATG GAG GGC GGC CTT CTG GAC AAG CCA GAC AAC TGT CCT GAC      3748

ATG CTG TTT GAA CTG ATG CGC ATG TGC TGG CAG TAT AAC CCC AAG ATG      3796

AGG CCT TCC TTC CTG GAG ATC ATC AGC AGC ATC AAA GAG GAG ATG GAG      3844

CCT GGC TTC CGG GAG GTC TCC TTC TAC TAC AGC GAG GAG AAC AAG CTG      3892

CCC GAG CCG GAG GAG CTG GAC CTG GAG CCA GAG AAC ATG GAG AGC GTC      3940

CCC CTG GAC CCC TCG GCC TCC TCG TCC TCC CTG CCA CTG CCC GAC AGA      3988

CAC TCA GGA CAC AAG GCC GAG AAC GGC CCC GGC CCT GGG GTG CTG GTC      4036
```

```
CTC CGC GCC AGC TTC GAC GAG AGA CAG CCT TAC GCC CAC ATG AAC GGG    4084

GGC CGC AAG AAC GAG CGG GCC TTG CCG CTG CCC CAG TCT TCG ACC TGC    4132

TGATCCTTGG ATCCTGAATC TGTGCAAACA GTAACGTGTG CGCACGCGCA GCGGGTGGG   4192

GGGGGAGAGA GAGTTTTAAC AATCCATTCA CAAGCCTCCT GTACCTCAGT GGATCTTCAG  4252

TTCTGCCCTT GCTGCCCGCG GGAGACAGCT TCTCTGCAGT AAAACACATT TGGGATGTTC  4312

CTTTTTTCAA TATGCAAGCA GCTTTTTATT CCCTGCCCAA ACCCTTAACT GACATGGGCC  4372

TTTAAGAACC TTAATGACAA CACTTAATAG CAACAGAGCA CTTGAGAACC AGTCTCCTCA  4432

CTCTGTCCCT GTCCTTCCCT GTTCTCCCTT TCTCTCTCCT CTCTGCTTCA TAACGGAAAA  4492

ATAATTGCCA CAAGTCCAGC TGGGAAGCCC TTTTTATCAG TTTGAGGAAG TGGCTGTCCC  4552

TGTGGCCCCA TCCAACCACT GTACACACCC GCCTGACACC GTGGGTCATT ACAAAAAAAC  4612

ACGTGGAGAT GGAAATTTTT ACCTTTATCT TTCACCTTTC TAGGGACATG AAATTTACAA  4672

AGGGCCATCG TTCATCCAAG GCTGTTACCA TTTTAACGCT GCCTAATTTT GCCAAAATCC  4732

TGAACTTTCT CCCTCATCGG CCCGGCGCTG ATTCCTCGTG TCCGGAGGCA TGGGTGAGCA  4792

TGGCAGCTGG TTGCTCCATT TGAGAGACAC GCTGGCGACA CACTCCGTCC ATCCGACTGC  4852

CCCTGCTGTG CTGCTCAAGG CCACAGGCAC ACAGGTCTCA TTGCTTCTGA CTAGATTATT  4912

ATTTGGGGGA ACTGGACACA ATAGGTCTTT CTCTCAGTGA AGGTGGGGAG AAGCTGAACC  4972

GGC                                                                4975
```

(2) INFORMATION FOR SEQ ID NO:2:

(i) SEQUENCE CHARACTERISTICS:
        (A) LENGTH: 1367 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Lys Ser Gly Ser Gly Gly Ser Pro Thr Ser Leu Trp Gly Leu
-30             -25                 -20                 -15

Leu Phe Leu Ser Ala Ala Leu Ser Leu Trp Pro Thr Ser Gly Glu Ile
                -10                 -5                  1

Cys Gly Pro Gly Ile Asp Ile Arg Asn Asp Tyr Gln Gln Leu Lys Arg
        5                   10                  15

Leu Glu Asn Cys Thr Val Ile Glu Gly Tyr Leu His Ile Leu Leu Ile
    20                  25                  30

Ser Lys Ala Glu Asp Tyr Arg Ser Tyr Arg Phe Pro Lys Leu Thr Val
35              40                  45                  50

Ile Thr Glu Tyr Leu Leu Leu Phe Arg Val Ala Gly Leu Glu Ser Leu
                55                  60                  65

Gly Asp Leu Phe Pro Asn Leu Thr Val Ile Arg Gly Trp Lys Leu Phe
                70                  75                  80

Tyr Asn Tyr Ala Leu Val Ile Phe Glu Met Thr Asn Leu Lys Asp Ile
                85                  90                  95

Gly Leu Tyr Asn Leu Arg Asn Ile Thr Arg Gly Ala Ile Arg Ile Glu
                100                 105                 110

Lys Asn Ala Asp Leu Cys Tyr Leu Ser Thr Val Asp Trp Ser Leu Ile
115                 120                 125                 130

Leu Asp Ala Val Ser Asn Asn Tyr Ile Val Gly Asn Lys Pro Pro Lys
                135                 140                 145
```

-continued

Glu Cys Gly Asp Leu Cys Pro Gly Thr Met Glu Glu Lys Pro Met Cys
            150                 155                 160

Glu Lys Thr Thr Ile Asn Asn Glu Tyr Asn Tyr Arg Cys Trp Thr Thr
            165                 170                 175

Asn Arg Cys Gln Lys Met Cys Pro Ser Thr Cys Gly Lys Arg Ala Cys
            180                 185                 190

Thr Glu Asn Asn Glu Cys Cys His Pro Glu Cys Leu Gly Ser Cys Ser
195                 200                 205                 210

Ala Pro Asp Asn Asp Thr Ala Cys Val Ala Cys Arg His Tyr Tyr Tyr
                215                 220                 225

Ala Gly Val Cys Val Pro Ala Cys Pro Pro Asn Thr Tyr Arg Phe Glu
            230                 235                 240

Gly Trp Arg Cys Val Asp Arg Asp Phe Cys Ala Asn Ile Leu Ser Ala
            245                 250                 255

Glu Ser Ser Asp Ser Glu Gly Phe Val Ile His Asp Gly Glu Cys Met
            260                 265                 270

Gln Glu Cys Pro Ser Gly Phe Ile Arg Asn Gly Ser Gln Ser Met Tyr
275                 280                 285                 290

Cys Ile Pro Cys Glu Gly Pro Cys Pro Lys Val Cys Glu Glu Glu Lys
                295                 300                 305

Lys Thr Lys Thr Ile Asp Ser Val Thr Ser Ala Gln Met Leu Gln Gly
            310                 315                 320

Cys Thr Ile Phe Lys Gly Asn Leu Leu Ile Asn Ile Arg Arg Gly Asn
            325                 330                 335

Asn Ile Ala Ser Glu Leu Glu Asn Phe Met Gly Leu Ile Glu Val Val
340                 345                 350

Thr Gly Tyr Val Lys Ile Arg His Ser His Ala Leu Val Ser Leu Ser
355                 360                 365                 370

Phe Leu Lys Asn Leu Arg Leu Ile Leu Gly Glu Glu Gln Leu Glu Gly
            375                 380                 385

Asn Tyr Ser Phe Tyr Val Leu Asp Asn Gln Asn Leu Gln Gln Leu Trp
            390                 395                 400

Asp Trp Asp His Arg Asn Leu Thr Ile Lys Ala Gly Lys Met Tyr Phe
            405                 410                 415

Ala Phe Asn Pro Lys Leu Cys Val Ser Glu Ile Tyr Arg Met Glu Glu
            420                 425                 430

Val Thr Gly Thr Lys Gly Arg Gln Ser Lys Gly Asp Ile Asn Thr Arg
435                 440                 445                 450

Asn Asn Gly Glu Arg Ala Ser Cys Glu Ser Asp Val Leu His Phe Thr
                455                 460                 465

Ser Thr Thr Thr Ser Lys Asn Arg Ile Ile Ile Thr Trp His Arg Tyr
            470                 475                 480

Arg Pro Pro Asp Tyr Arg Asp Leu Ile Ser Phe Thr Val Tyr Tyr Lys
            485                 490                 495

Glu Ala Pro Phe Lys Asn Val Thr Glu Tyr Asp Gly Gln Asp Ala Cys
500                 505                 510

Gly Ser Asn Ser Trp Asn Met Val Asp Val Asp Leu Pro Pro Asn Lys
515                 520                 525                 530

Asp Val Glu Pro Gly Ile Leu Leu His Gly Leu Lys Pro Trp Thr Gln
            535                 540                 545

Tyr Ala Val Tyr Val Lys Ala Val Thr Leu Thr Met Val Glu Asn Asp
            550                 555                 560

His Ile Arg Gly Ala Lys Ser Glu Ile Leu Tyr Ile Arg Thr Asn Ala
            565                 570                 575

```
Ser Val Pro Ser Ile Pro Leu Asp Val Leu Ser Ala Ser Asn Ser Ser
    580              585                  590

Ser Gln Leu Ile Val Lys Trp Asn Pro Pro Ser Leu Pro Asn Gly Asn
595              600              605                  610

Leu Ser Tyr Tyr Ile Val Arg Trp Gln Arg Gln Pro Gln Asp Gly Tyr
                615              620              625

Leu Tyr Arg His Asn Tyr Cys Ser Lys Asp Lys Ile Pro Ile Arg Lys
            630              635                  640

Tyr Ala Asp Gly Thr Ile Asp Ile Glu Glu Val Thr Glu Asn Pro Lys
        645              650              655

Thr Glu Val Cys Gly Gly Glu Lys Gly Pro Cys Cys Ala Cys Pro Lys
    660              665              670

Thr Glu Ala Glu Lys Gln Ala Glu Lys Glu Glu Ala Glu Tyr Arg Lys
675              680              685                  690

Val Phe Glu Asn Phe Leu His Asn Ser Ile Phe Val Pro Arg Pro Glu
            695              700              705

Arg Lys Arg Arg Asp Val Met Gln Val Ala Asn Thr Thr Met Ser Ser
            710              715              720

Arg Ser Arg Asn Thr Thr Ala Ala Asp Thr Tyr Asn Ile Thr Asp Pro
        725              730              735

Glu Glu Leu Glu Thr Glu Tyr Pro Phe Phe Glu Ser Arg Val Asp Asn
    740              745              750

Lys Glu Arg Thr Val Ile Ser Asn Leu Arg Pro Phe Thr Leu Tyr Arg
755              760              765                  770

Ile Asp Ile His Ser Cys Asn His Glu Ala Glu Lys Leu Gly Cys Ser
            775              780              785

Ala Ser Asn Phe Val Phe Ala Arg Thr Met Pro Ala Glu Gly Ala Asp
        790              795              800

Asp Ile Pro Gly Pro Val Thr Trp Glu Pro Arg Pro Glu Asn Ser Ile
    805              810              815

Phe Leu Lys Trp Pro Glu Pro Glu Asn Pro Asn Gly Leu Ile Leu Met
    820              825              830

Tyr Glu Ile Lys Tyr Gly Ser Gln Val Glu Asp Gln Arg Glu Cys Val
835              840              845                  850

Ser Arg Gln Glu Tyr Arg Lys Tyr Gly Gly Ala Lys Leu Asn Arg Leu
            855              860              865

Asn Pro Gly Asn Tyr Thr Ala Arg Ile Gln Ala Thr Ser Leu Ser Gly
        870              875              880

Asn Gly Ser Trp Thr Asp Pro Val Phe Phe Tyr Val Gln Ala Lys Thr
    885              890              895

Gly Tyr Glu Asn Phe Ile His Leu Ile Ile Ala Leu Pro Val Ala Val
    900              905              910

Leu Leu Ile Val Gly Gly Leu Val Ile Met Leu Tyr Val Phe His Arg
915              920              925                  930

Lys Arg Asn Asn Ser Arg Leu Gly Asn Gly Val Leu Tyr Ala Ser Val
            935              940              945

Asn Pro Glu Tyr Phe Ser Ala Ala Asp Val Tyr Val Pro Asp Glu Trp
        950              955              960

Glu Val Ala Arg Glu Lys Ile Thr Met Ser Arg Glu Leu Gly Gln Gly
    965              970              975

Ser Phe Gly Met Val Tyr Glu Gly Val Ala Lys Gly Val Val Lys Asp
    980              985              990
```

```
Glu Pro Glu Thr Arg Val Ala Ile Lys Thr Val Asn Glu Ala Ala Ser
995                 1000                1005                1010

Met Arg Glu Arg Ile Glu Phe Leu Asn Glu Ala Ser Val Met Lys Glu
            1015                1020                1025

Phe Asn Cys His His Val Val Arg Leu Leu Gly Val Val Ser Gln Gly
            1030                1035                1040

Gln Pro Thr Leu Val Ile Met Glu Leu Met Thr Arg Gly Asp Leu Lys
            1045                1050                1055

Ser Tyr Leu Arg Ser Leu Arg Pro Glu Met Glu Asn Asn Pro Val Leu
1060                1065                1070

Ala Pro Pro Ser Leu Ser Lys Met Ile Gln Met Ala Gly Glu Ile Ala
1075                1080                1085                1090

Asp Gly Met Ala Tyr Leu Asn Ala Asn Lys Phe Val His Arg Asp Leu
            1095                1100                1105

Ala Ala Arg Asn Cys Met Val Ala Glu Asp Phe Thr Val Lys Ile Gly
            1110                1115                1120

Asp Phe Gly Met Thr Arg Asp Ile Tyr Glu Thr Asp Tyr Tyr Arg Lys
            1125                1130                1135

Gly Gly Lys Gly Leu Leu Pro Val Arg Trp Met Ser Pro Glu Ser Leu
            1140                1145                1150

Lys Asp Gly Val Phe Thr Thr Tyr Ser Asp Val Trp Ser Phe Gly Val
1155                1160                1165                1170

Val Leu Trp Glu Ile Ala Thr Leu Ala Glu Gln Pro Tyr Gln Gly Leu
            1175                1180                1185

Ser Asn Glu Gln Val Leu Arg Phe Val Met Glu Gly Gly Leu Leu Asp
            1190                1195                1200

Lys Pro Asp Asn Cys Pro Asp Met Leu Phe Glu Leu Met Arg Met Cys
1205                1210                1215

Trp Gln Tyr Asn Pro Lys Met Arg Pro Ser Phe Leu Glu Ile Ile Ser
1220                1225                1230

Ser Ile Lys Glu Glu Met Glu Pro Gly Phe Arg Glu Val Ser Phe Tyr
1235                1240                1245                1250

Tyr Ser Glu Glu Asn Lys Leu Pro Glu Pro Glu Glu Leu Asp Leu Glu
            1255                1260                1265

Pro Glu Asn Met Glu Ser Val Pro Leu Asp Pro Ser Ala Ser Ser Ser
            1270                1275                1280

Ser Leu Pro Leu Pro Asp Arg His Ser Gly His Lys Ala Glu Asn Gly
            1285                1290                1295

Pro Gly Pro Gly Val Leu Val Leu Arg Ala Ser Phe Asp Glu Arg Gln
            1300                1305                1310

Pro Tyr Ala His Met Asn Gly Gly Arg Lys Asn Glu Arg Ala Leu Pro
1315                1320                1325                1330

Leu Pro Gln Ser Ser Thr Cys
            1335
```

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: Genomic DNA (xi) SEQUENCE DESCRIPTION: SEQ ID NO:3:

```
CTGGGGAATG CTGTGCTGTA T                                      21
```

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: Genomic DNA (xi) SEQUENCE DESCRIPTION: SEQ ID NO:4:

AATGGAGTGC TAGCTGCCTC TGTG                      24

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: Genomic DNA (xi) SEQUENCE DESCRIPTION: SEQ ID NO:5:

AACCCGGAGT GTTTCAGCGC T                        21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: Genomic DNA (xi) SEQUENCE DESCRIPTION: SEQ ID NO:6:

AACCCGGAGT CATTCAGCGC T                        21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: Genomic DNA (xi) SEQUENCE DESCRIPTION: SEQ ID NO:7:

AACCCGGAGG CTTTCAGCGC T                        21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: Genomic DNA (xi) SEQUENCE DESCRIPTION: SEQ ID NO:8:

AACCCGGAGC TATTCAGCGC T                        21

(2) INFORMATION FOR SEQ ID NO:9:

(i) SEQUENCE CHARACTERISTICS:

(A) LENGTH: 21 base pairs
    (B) TYPE: nucleic acid
    (C) STRANDEDNESS: single
    (D) TOPOLOGY: unknown (ii) MOLECULE TYPE: Genomic DNA (xi) SEQUENCE DESCRIPTION: SEQ ID NO:9:

AACCCGGAGA CATTCAGCGC T                                         21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: Genomic DNA (xi) SEQUENCE DESCRIPTION: SEQ ID NO:10:

GCTGATGTGG CTGTTCCTGA T                                         21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: Genomic DNA (xi) SEQUENCE DESCRIPTION: SEQ ID NO:11:

GTGGCCATTG CTACAGTGAA C                                         21

(2) INFORMATION FOR SEQ ID NO:12:

(i) SEQUENCE CHARACTERISTICS:
        (A) LENGTH: 39 base pairs
        (B) TYPE: nucleic acid
        (C) STRANDEDNESS: single
        (D) TOPOLOGY: unknown (ii) MOLECULE TYPE: Genomic DNA (xi) SEQUENCE DESCRIPTION: SEQ ID NO:12:

GGGAATGGAG TGCTGTATCG GGAGAAGATC ACCATGAGC                      39

(2) INFORMATION FOR SEQ ID NO:13:

(i) SEQUENCE CHARACTERISTICS:
        (A) LENGTH: 12 base pairs
        (B) TYPE: nucleic acid
        (C) STRANDEDNESS: single
        (D) TOPOLOGY: unknown (ii) MOLECULE TYPE: Genomic DNA (xi) SEQUENCE DESCRIPTION: SEQ ID NO:13:

TGCTCTAGAG CA                                                   12

(2) INFORMATION FOR SEQ ID NO:14:

(i) SEQUENCE CHARACTERISTICS:
        (A) LENGTH: 150 base pairs
        (B) TYPE: nucleic acid
        (C) STRANDEDNESS: single
        (D) TOPOLOGY: unknown (ii) MOLECULE TYPE: Genomic DNA (xi) SEQUENCE DESCRIPTION: SEQ ID NO:14:

GCAGGATGCC TGCGGCTCCA ACAGCTGGAA CATGGTGGAC GTGGACCTCC CGCCCAACAA    60

GGACGTGGAG CCCGGCATCT TACTACATGG GCTGAAGCCC TGGACTCAGT ACGCCGTTTA   120

CGTCAAGGCT GTGACCCTCA CCATGGTGGA                                    150